(12) United States Patent
Smith

(10) Patent No.: US 11,957,837 B2
(45) Date of Patent: Apr. 16, 2024

(54) METHOD TO REDUCE SLOSH ENERGY ABSORPTION AND ITS DAMAGING EFFECTS THROUGH THE REDUCTION OF INELASTIC COLLISIONS IN AN ORGANISM

(71) Applicant: David Smith, Richmond, IN (US)

(72) Inventor: David Smith, Richmond, IN (US)

( * ) Notice: Subject to any disclaimer, the term of this patent is extended or adjusted under 35 U.S.C. 154(b) by 1733 days.

(21) Appl. No.: 15/968,149

(22) Filed: May 1, 2018

(65) Prior Publication Data

US 2018/0333159 A1   Nov. 22, 2018

Related U.S. Application Data

(63) Continuation-in-part of application No. 14/620,369, filed on Feb. 12, 2015, now Pat. No. 9,987,020, which
(Continued)

(51) Int. Cl.
*A61M 16/00* (2006.01)
*A41D 13/05* (2006.01)
(Continued)

(52) U.S. Cl.
CPC ..... *A61M 16/0045* (2013.01); *A41D 13/0512* (2013.01); *A61B 17/132* (2013.01);
(Continued)

(58) Field of Classification Search
CPC .. A61M 16/00; A61M 16/0045; A61M 16/06; A61M 16/10; A61M 16/12;
(Continued)

(56) References Cited

U.S. PATENT DOCUMENTS 5,511,544 A * 4/1996 McKenna ......... A61M 16/0045
128/205.13
5,983,891 A * 11/1999 Fukunaga ......... A61M 16/1055
128/914
(Continued)

OTHER PUBLICATIONS

Ailiang, Xie, et al., "Effects of inhaled CO2 and added dead space on idiopathic central sleep apnea," 1997 American Physiological Society (9 pages).
(Continued)

*Primary Examiner* — Colin W Stuart
(74) *Attorney, Agent, or Firm* — Maginot, Moore & Beck, LLP

(57) ABSTRACT

A method is provided for reducing the risk of sustaining a traumatic brain injury caused by a traumatic event that includes identifying a subject at risk of sustaining a traumatic brain injury, and then precisely increasing the partial pressure of carbon-dioxide ($CO_2$) in the blood of the subject ($pCO_2$). This method can be applied to raise the $CO_2$ and $pCO_2$ to improve orthostatic hypotension in conditions such as dysautonomias (like Positional Orthostatic Tachycardic Syndrome POTS) and to facilitate the drive to breathe in conditions like Central Sleep Apnea (CSA) and Sudden Infant Death Syndrome (SIDS). The $pCO_2$ of the person is increased by placing a breathing apparatus over the mouth of the person through which the person must breath, wherein the breathing apparatus includes an enlarged dead space volume in which expired $CO_2$ collects to be inhaled or re-breathed by the person on the next inhalation.

13 Claims, 21 Drawing Sheets

Related U.S. Application Data is a continuation of application No. 12/807,677, filed on Sep. 10, 2010, now Pat. No. 8,985,120.

(60) Provisional application No. 61/260,313, filed on Nov. 11, 2009, provisional application No. 61/241,625, filed on Sep. 11, 2009.

(51) Int. Cl.
| | |
|---|---|
| *A61B 17/132* | (2006.01) |
| *A61B 90/00* | (2016.01) |
| *A61F 5/058* | (2006.01) |
| *A61F 5/30* | (2006.01) |
| *A61M 16/06* | (2006.01) |
| *A61M 16/10* | (2006.01) |
| A61K 31/07 | (2006.01) |
| A61K 31/573 | (2006.01) |
| A61K 31/65 | (2006.01) |

(52) U.S. Cl.
CPC .......... *A61B 90/00* (2016.02); *A61F 5/05883* (2013.01); *A61F 5/30* (2013.01); *A61M 16/06* (2013.01); *A61M 16/10* (2013.01); *A61B 17/1322* (2013.01); *A61B 17/1325* (2013.01); *A61B 2090/063* (2016.02); *A61B 2090/064* (2016.02); *A61B 2090/0807* (2016.02); *A61K 31/07* (2013.01); *A61K 31/573* (2013.01); *A61K 31/65* (2013.01); *A61M 16/0683* (2013.01)

(58) Field of Classification Search
CPC .. A61M 2016/0661; A61M 2202/0225; A61M 2205/58; A61M 2205/583; A62B 18/00; A62B 18/02; A62B 18/025

See application file for complete search history.

(56) References Cited

U.S. PATENT DOCUMENTS

| | | | |
|---|---|---|---|
| 6,408,848 B1 * | 6/2002 | Feldman | A61M 16/0045 128/200.22 |
| 7,886,740 B2 | 2/2011 | Thomas et al. | |
| 2002/0170561 A1 * | 11/2002 | Downey | A63B 69/00 128/205.12 |
| 2004/0216740 A1 * | 11/2004 | Remmers | A61M 16/085 128/204.18 |
| 2004/0216743 A1 * | 11/2004 | Orr | A61M 16/0093 128/205.12 |
| 2006/0130839 A1 * | 6/2006 | Bassovitch | A61M 16/0045 128/914 |
| 2007/0240718 A1 * | 10/2007 | Daly | A61M 16/08 128/204.22 |
| 2009/0133696 A1 * | 5/2009 | Remmers | A61M 16/0493 128/204.26 |

OTHER PUBLICATIONS

Shokoueinejad, Mehdi, et al., "A Modeling Study on Inspired CO2 Rebreathing Device for Sleep Apnea Treatment by Means of CFD Analysis and Experiment," J. Med. Bio. Eng. (2017) 37:288-297, (10 pages).

Steens, Rodney D., et al., "Effect of Inhaled 3% CO2, on Cheyne-Stokes Respiration in Congestive Heart Failure," Sleep, 17(1):61-68, 1994 American Sleep Disorders Association and Sleep Research Society. (8 pages).

Emedicalupdates.com., "Non-rebreather mask v. Partial rebreather mask v. Simple mask," published on Nov. 26, 2017 by Editorial Team (7 pages).

\* cited by examiner

METHOD TO REDUCE SLOSH ENERGY ABSORPTION AND ITS DAMAGING EFFECTS THROUGH THE REDUCTION OF INELASTIC COLLISIONS IN AN ORGANISM

CROSS-REFERENCE TO RELATED APPLICATIONS

This application is a continuation-in-part of U.S. application Ser. No. 14/620,369, filed on Feb. 12, 2015, which is a continuation of U.S. application Ser. No. 12/807,677 (now issued as U.S. Pat. No. 8,985,120), filed Sep. 10, 2010, which claims priority from provisional application No. 61/241,625 filed on Sep. 11, 2009 and provisional application No. 61/260,313 filed on Nov. 11, 2009. The disclosures of these applications are incorporated herein by reference.

BACKGROUND

When liquid in a tank or vessel experiences dynamic motion, a variety of wave interactions and liquid phenomena can exist. The oscillation of a fluid caused by external force, called sloshing, occurs in moving vessels containing liquid masses, such as trucks, aircraft, and liquid fueled rockets. This sloshing effect can be a severe problem in energy absorption, and thus, vehicle stability and control.

Living beings can experience analogous sloshing, such as in the skull under impact due to collisions or blast impacts. TBI (Traumatic Brain Injury) is the leading cause of death in individuals under age 45. The number of people diagnosed annually with TBI exceeds HIV/ADS, multiple sclerosis, spinal cord injury. Alzheimer's, and breast cancer combined. The cost of TBI in the U.S. is estimated at anywhere from $50 to $150 billion, but quantifying the cost of the pain and suffering of the victims and their families is difficult. The January, 2008 New England Journal of Medicine reports: "More than 1.75 million U.S. military personnel have deployed to Iraq or Afghanistan since the start of military operations in 2001. Because of improved protective equipment, a higher percentage of soldiers are surviving injuries that would have been fatal in previous wars. Head and neck injuries, including severe brain trauma, have been reported in one quarter of service members who have been evacuated from Iraq and Afghanistan". Traumatic brain injury has been labeled a "signature injury" of the wars in Iraq and Afghanistan. The exact proportion of troops who have traumatic brain injury is not known, although it has been reported to be as high as 18% in news articles citing army medical officials. Many troops reportedly have persistent post-concussive symptoms, such as irritability, memory problems, headache, and difficulty concentrating.

The mitigation of blast wave and collision damage is based largely on the principle of energy absorption of fluid-filled containers. As there becomes more room for movement within a vessel, more energy can be absorbed (slosh) rather than transported through the vessel. To reduce this energy absorption, one must attempt to more closely approximate elastic collisions. Elastic collisions are those that result in no net transfer of energy—chiefly, acoustic, kinetic, vibrational, or thermal energy (also stated as a coefficient of restitution (r) approximating 1.0).

Nature's creatures use many mechanisms to abate Traumatic Brain Injury through mitigating SLOSH and thus external energy absorption demonstrating incredible g-force tolerance. Woodpeckers have restricted axial globe movement of their eyes and don't even possess sinus cavities in their heads to reduce SLOSH, thus allowing tolerances of up to 1500 Gs while impacting trees. All avian species retain the nucleuses of their erythrocytes and thus have markedly less distensible red blood cells thus mitigating SLOSH. Longhorn, head butting, sheep also have diminished distensibility of their red blood cells and maintain an elevated pH in their circulatory stream by adding dead space to their respiratory outflow tract. Bats sleep upside down to increase the cerebral space occupying capability of their blood and have arterial venous shunts in their wings to maintain control over $CO_2$. Highly G-force tolerant insects maintain tight control over $CO_2$ through spiracles in the sides of their thorax and abdomen, and aquatic mammals maintain large reservoirs of $CO_2$ partly through large air sacs attached to their respiratory tree.

Although the skull, blood, and brain of a human are nearly incompressible, the volume of the vasculature tree of the cerebrum is actually quite reactive and malleable. As volume is added to the cranium and spinal column, increased pressure follows. The pressure volume curve shown in FIG. 1 demonstrates that the compliance of the cerebral-spinal system can be "filled up" with mildly increasing cerebral volume. The less "compliant" the system is (i.e., the more volume that is added) the less slosh energy that can be absorbed. This added pressure and volume would be similar to the added pressure and volume of airbags and seat-belts to the compartment of a vehicle. Devices that reduce slosh, such as air bags, combined with lap and shoulder safety belts, offer the most effective safety protection available today for vehicle passenger occupants. As seat belts are 57% effective in preventing traumatic and fatal brain injuries, one might reasonably expect a favorable result when constraining the objects within a cranial compartment.

Increasing cerebral blood volume and pressure safely and reversibly would serve to fill up the compliance of the cerebral vascular tree and thus reduce the ability to absorb external energies through slosh energy absorption. Envisioning the skull as a container with two major arterial passages entering and four major venous pathways exiting, then any process that either increases the arterial flow, or impedes venous outflow, will serve to fill up the container to its confines. With the application of measured pressure to the neck, the cranial-spinal blood volume increases rapidly and plateaus at a new higher level. Total cerebral blood flow is not affected by diverting venous outflow of blood from jugulars to the vertebral vessels of the brain. The blood volume venous pressure relationship shows a diminishing increase in volume with each increment of neck pressure over the range 40 to 70 mm of mercury. It is of interest that the cranial blood pressure increases from 10 to 30 percent. The cerebral spinal fluid pressure responds on compression of the individual jugular veins. The average rise in certain tests was 30-45%. Jugular compression increases cerebral blow flow to a new plateau in as little as 0.5 seconds. Increasing the arterial blood flow velocity would also serve to increase the intra-cranial pressure (ICP) and volume, and ultimately raise the end-tidal $CO_2$ ($ETCO_2$) by 10% which has been shown to increase the middle cerebral artery blood flow velocity by 40%. This degree of cranial blood volume and pressure increase would be very beneficial in slosh mitigation.

Further, safety of such a procedure of venous compression is well known. In particular, it is known that compression of the neck does not interfere with arterial flow into the cranium and increasing $ETCO_2$ (with resultant rises in arterial flow velocity) does not alter the venous outflow tracts. Although the venous jugular flow beneath the pressure cuff may be temporarily halted, the venous outflow from the cranium is never completely stopped, particularly from the anastomosis between the vertebral spinal vein and the basilar plexus and occipital sinuses which are incompressible. There was no correlation between EEG changes and changes in systolic blood pressure occurring during vascular compression. Compression of up to 70 mmHg does not affect cardiac output, arteriolar blood pressure, pulse rate, or urine flow.

SUMMARY OF THE DISCLOSURE

In one aspect of the disclosure, a method is provided for reducing the risk of sustaining a traumatic brain injury caused by a traumatic event comprising the steps of identifying a subject at risk of sustaining a traumatic brain injury, and then increasing the partial pressure of carbon-dioxide ($CO_2$) in the blood of the subject ($pCO_2$). In another aspect of the disclosure, the rise in $CO_2$ is expected to improve (or lower) the compensatory reserve volume of the cranium, thus improving the symptoms of many dysautonomias such as Positional Orthostatic Tachycardia Syndrome (POTS). A rise in $ETCO_2$ by this mechanism would also have utility in improving the respiratory drive in Central Sleep Apnea (CSA) and Sudden Infant Death Syndrome (SIDS) and even mitigating the symptoms of migraine sufferers.

In another aspect of the disclosure, a breathing apparatus is provided for increasing the partial pressure of carbon-dioxide ($CO_2$) in the blood of a subject ($pCO_2$), that comprises a chamber having an opening in communication with the mouth of the subject and at least one outlet through which gas flows as the subject inhales and exhales, and an enlarged dead space between the opening in communication with the mouth and the at least one outlet. The dead space defines a volume sized to retain a predetermined portion of the $CO_2$ exhaled by the subject to be inhaled or re-breathed by the subject on the next inhalation. In accordance with the present disclosure, the dead space does not exchange $CO_2$ or $O_2$ with the body. The breathing apparatus includes a portion for retaining the breathing apparatus in communication with the mouth of the subject, such as a strap arrangement or a mouthpiece.

In one feature, the dead space is adjustable or calibrated to the physiology of the subject, and in particular to the tidal volume of air displaced by the subject during inhalation and exhalation. In particular, the dead space is calibrated to the weight of the subject.

Breathing through the nasal passage in effect produces a dead space volume, which can amount to almost 150 ml of volume in an average adult. However, this anatomic "dead space" is not easily available for rebreathing as it resides in the many tributaries such as the para-nasal sinuses, middle ear space and mastoid air cells. To circulate the $CO_2$ out of these spaces, the tributaries include turbinates to generate turbulent flow which provides for mixing of the passage and sinus flow and thus accessing the $CO_2$ residing there.

Switching from mouth breathing to nasal breathing is theorized to be a method for the body to exert control over the total utilized dead space and thus $CO_2$ levels maintained within the body. Further control is effectuated by the Nasal Cycle, a little known or understood reflex (that all, or nearly all, vertebrates appear to possess) whereby vascular engorgement of one of the two nasal orifices is brought about through activation of the sympathetic nervous system originating in the thoracic spinal cord. When one side of the nasal passage closes, the nasal resistance soars and the tendency is to open one's mouth to ease the work of breathing. Active, yet not conscious, control of the body's $CO_2$ levels could be triggered by the rate and duration of the vascular engorgement of nasal pathway and, at least in humans, this reflex has been shown to actively engorge one side or the other approximately every 1-8 hours. Tracing the neural control of this reflex appears to put the neural pathway inside the sympathetic nervous system originating in the upper one third of the spinal cord. This location is interesting as no chemoreceptor (for monitoring for $CO_2$ levels) is known in this region. It should be noted that the pressure and volume change dramatically inside the spinal column and baroreceptors (pressure sensitive monitors) within this space could also maintain control of the Nasal Reflex with subsequent vascular congestion in the nares.

The scientific and lay scientific communities have long observed benefits to nasal breathing over oral breathing and studies have been undertaken to understand why. Studies by Fink et al and reported by Tanaka describe an increase in the End-tidal $CO_2$ ($ETCO_2$) level of the body by 1.5 mmHg by the mere act of closing one's mouth and breathing through the nose. See, Fink, B. R., E. C. Hanks, S. H. Ngai, and E. M. Papper, Central Regulation of Respiration during Anesthesia and Wakefulness, *Ann of NY Acad of Science*, 109: 892-900, 1963; and Tanaka, An Assessment of Nasal Functions in Control of Nasal Breathing, Department of Surgery, Institute of Pulmonary Cancer Research, and Department of Physiology, School of Medicine, Chiba University, Chiba 280, Japan, the disclosures of which are incorporated in their entirety by reference. As stated above, the added dead space volume in an average 70 kg adult breathing through the nose is about 150 ml, which unit of volume can be referred to as a "Physiological Breathing Unit (PBU)". The PBU can be considered to be the minimum volume of added dead space that may provide a demonstrable beneficial physiological alteration to occur in the body. $CO_2$ added to the human body can be described as multiples of PBU (for adults 150 ml, and for infants, 3 ml).

$CO_2$ is the major determinant of intracranial volume and pressure and also dictates the middle cerebral artery (MCA) blood velocity. A modest increase of fractional inspiration of $CO_2$ ($FICO_2$), for example 5%, leads to an increase in MCA velocity of 50%.

The present disclosure contemplates a method for treating a condition of a subject that is responsive changes in intracranial pressure and/or middle cerebral blood velocity. The condition can be a potential or actual traumatic brain injury. The method comprises increasing the partial pressure of carbon-dioxide ($CO_2$) in the blood of the subject ($pCO_2$). In one aspect, this increase in $pCO_2$ is accomplished by increasing the $CO_2$ content of the air inhaled by the subject above the ambient $CO_2$ content of the air, and in particular by forcing the subject to rebreathe a predetermined portion of the $CO_2$ exhaled by the subject while inhaling ambient air. The predetermined portion of exhaled $CO_2$ is calibrated according to the physiological attributes to the subject indicative of tidal volume, such as weight. In one aspect, the rebreathing is accomplished by a rebreathing apparatus with an enlarged dead space calibrated to retain the predetermined portion of exhaled $CO_2$ to be rebreathed on the next inhalation of ambient air. In one feature of this disclosure, the apparatus can incorporate means to adjust the dead space volume as needed for the subject.

DETAILED DESCRIPTION

Figure 1:
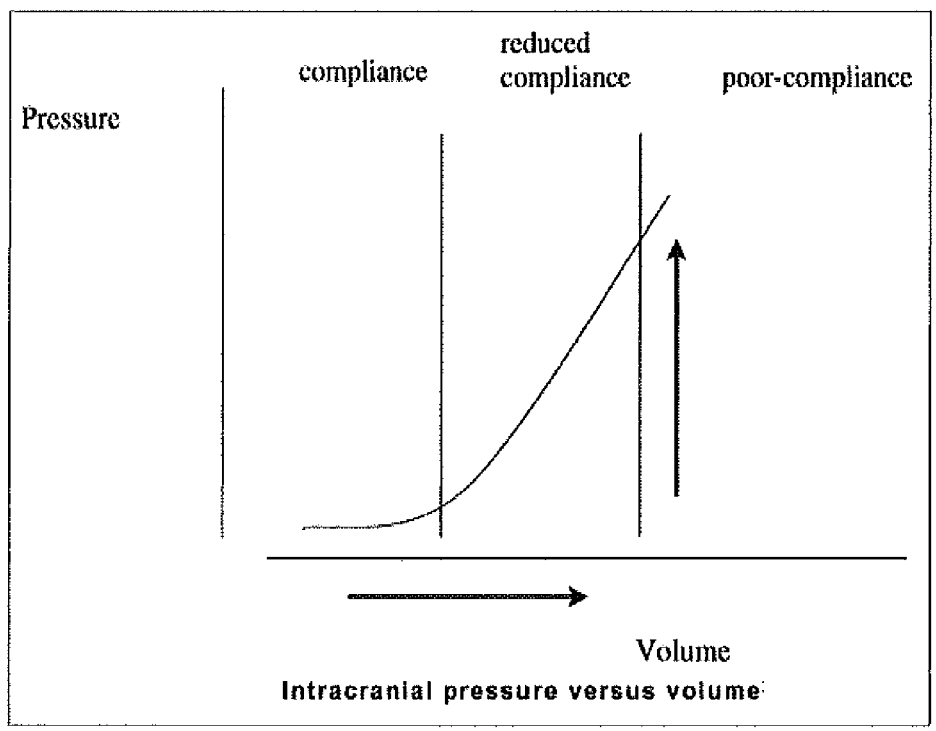
FIG. 1 is a graph of intracranial pressure as a function of intracranial volume.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains Various embodiments described below may locally alter, elevate, or temporarily maintain an altered physiology of an organism to reduce the likelihood of energy absorption through slosh whereby the coefficient of restitution (r) is increased. The coefficient of restitution (r) indicates the variance of an impacting object away from being a complete total elastic collision (an (r) of 1.0=no energy transfer). Blast or energy absorption in an organism can be viewed as a collision of bodies and thus be defined by a transfer of energies through elastic or inelastic collisions. The mechanisms for biological fluids and molecules to absorb energy can thus be identified and the resultant means to mitigate that absorption can be achieved through several slosh reducing techniques. Dissipation of energies post-blast is also potentiated through these techniques.

An effort to reduce the available space for movement of the brain by increasing cerebral blood volume can serve the purpose of mitigating Traumatic Brain Injury (TBI) or increasing orthostatic or G-tolerance through slosh mitigation at a tissue or organ (macro slosh) level. Red blood cells (RBC) or erythrocytes are highly distensible and have a "sloshable" volume to surface area of only 60 percent. Distending or stiffening these erythrocytes can reduce slosh within the individual cells at a cellular (micro slosh) level and thus reduce energy absorption upon collision. Molecules themselves have a three dimensionality and can have a lack of cross-bridging providing for floppy conformational changes that can promote slosh. Several mechanisms disclosed can safely and reversibly alter the conformational state of certain structures, cells and molecules in the circulatory system that will then reduce energy absorption through slosh at a molecular (molecular slosh) level. Elevating the local $CO_2$ and hence lowering the pH environment of an organism can also serve to mitigate slosh.

Raised inspired $CO_2$ (hypercapnia) can mitigate TBI through the reduction of macro slosh inside the cranium, but also has the ability to reduce the micro slosh inside each individual RBC and reduce the molecular slosh of each individual hemoglobin molecule. Each of these physiology changes allows a better passage of imparted forces through the blood and brain tissues with less of the forces being absorbed. Within the brain's more than 150 cc of cerebral blood, there are more than 1,000,000,000,000 erythrocytes (1 trillion cells) that hypercapnia can potentiate to more closely approximate elastic collisions of cells thus reducing the blast or collision energy absorption. Further, a hypercapnic state can also potentiate the collisions of all the hemoglobin molecules present in the cranium and body to be more elastic, thus reducing blast or collision energy absorption. There are 80 trillion RBC in the human body, more than one trillion in the brain space at any one time. All of these cells are susceptible to slosh energy absorption, and that absorption would be reduced in the setting of hypercapnia. Further, there are 240 million molecules of hemoglobin inside each RBC. Consequently, there are thus $1.9 \times 10^{22}$ hemoglobin molecules which are able to absorb the energies of a blast. The slosh energy absorption of these molecules can be significantly reduced by hypercapnia altering the molecules to approximate more elastic collisions.

Hemoglobin is made up of four iron containing heme components and four globins that surround (pocket) each heme, and in essence waterproof these hemes. If the blast energies are absorbed by fluids and blood cells, they are preferentially absorbed by hemoglobin which is then conformationally altered to allow water to enter the hemepocket leading to a rapid, catalytic oxidation to methemoglobin and superoxide. Superoxide is oxygen with an extra electron; methemoglobin is merely an oxyhemoglobin devoid of a superoxide. Without this extra electron, methemoglobin does not have the ability to carry or transfer oxygen (thus the brain suffocates), and in the case of blast lung, massive levels of methemoglobin have been recorded. The erythrocytes can slowly reduce methemoglobin back to functional hemoglobin but if this methemoglobin Reductase reaction is not capable of diverting adequate electrons to counter this redox chemistry, spillover occurs into the oxidative damaging formation of superoxide, nitric oxide, peroxinitrite, etc. When an electron moves from one molecule to another, the donor molecule is thus oxidized while the receiving molecule is reduced (hence the term "redox"). For decades methylene blue has been used as the incredibly safe and well tolerated antidote for cyanide poisoning (and methemoglobinemias). It safely and dramatically facilitates the reductive pathways of methhemoglobin back into hemoglobin. Hypercapnia not only pushes methylene blue into erythrocytes where it can be functional, but it also appears to actually drive methemoglobin reductase to more quickly convert methemoglobin back to hemoglobin. Further, the anti-oxidants (electron donors) ascorbic acid (vitamin C) and riboflavin are also driven into the erythrocyte by hypercapnia; These antioxidants are not useful for post blast or energy absorption outside of erythrocytes. A soldier or athlete can be given physiologic daily doses of Vitamin C, Riboflavin and methylene blue (not a vitamin) and upon triggering a need, hypercapnia will drive these cofactors into the erythrocyte where they can mitigate the after effects of blast energy absorption.

A first embodiment is a method to reduce slosh energy absorption through reduction of inelastic collisions in a fluid containing organism wherein the method is one or more of reversibly increasing pressure, or volume within the organs or cells, or reversibly altering vascular, molecular, or cell wall stiffness or configuration within said organism. One embodiment of a method to increase pressure within the cranium can be by temporarily raising the partial pressure of $CO_2$ ($pCO_2$) in the body of the organism by way of altering the fractional percentage of $CO_2$ inspired by the organism. Such a method can maintain the above hypercapnic inspired $CO_2$ levels to exceed ambient levels. The $CO_2$ is actively and instantly pumped into erythrocytes and after the external $CO_2$ delivery stops, the intracellular $CO_2$ levels may take hours to return to normal. These levels can be achieved and maintained by an externally imparted respiratory circuit which can modulate the fractional percentage of $CO_2$ inspired by the organism. The circuit could be one or more of a non-breathing circuit, a breath circuit mask, or a breathing circuit capable of organizing exhaled gas so as to modulate the fractional percentage of $CO_2$ inspired by the organism (a range from 0.05 to 100% could be utilized). The circuit can include a customizable re-breathing circuit whose dead space is adjustable based on an individual's weight and estimated tidal volume (i.e., the normal volume of air displaced between inhalation and exhalation), and desired or optimized level of hypercapnia (a $pCO_2$ range from 25 to 80 mmHg would be optimum). The mask or vessel can incorporate one or several dead space channels or tubes that provide an inhale and exhale pathway that superimpose each other and thereby create mixing of inspired and expired gases. Alternatively, a source of fresh gas, potentially containing $CO_2$ can be supplemented when capnography (measurement of exhaled end-tidal $CO_2$), if utilized, so indicates. A re-breathing respiratory circuit may have one or more of the following: a mask or collecting vessel which has one or multiple channels or tubes whose length or volume is rapidly adjustable to regulate the amount of dead space that an individual will re-breathe for the express purpose of raising or modulating their local $CO_2$ level within their blood stream. The circuit may also contain a physiologically insignificant amount of $CO_2$ in communication with a valve to be delivered to the patient, a fresh gas reservoir in communication with the source of fresh gas flow for receiving excess fresh gas not breathed by the patient, and a reserve gas supply in communication with the exit port through the valve and containing $CO_2$. Alternatively, a non-rebreathing circuit can be comprised of one or more of the following: a non-rebreathing valve preventing gas exhaled from the subject flowing into the circuit, a fresh gas source operative to supply a fresh gas containing physiologically insignificant amount of carbon dioxide to the subject through the non-rebreathing valve, and a reserved gas source operative to supply a reserved gas having a predetermined partial pressure of carbon dioxide to the subject through the non-rebreathing valve. These respiratory circuits can also be used to enable organisms to recover more quickly from vapor anesthetic administration, or poisoning with carbon monoxide, methanol, ethanol, or other volatile hydrocarbons. The circuit and method of treatment may also be used to reduce nitrogen levels in the body. These additional uses may require higher concentrations of oxygen than ambient air. In this case, the fresh gas could contain 100% oxygen and the reserve gas would contain 0.04-100% $CO_2$ and a high concentration of oxygen, for example 99.9 6-0%; although simply maintaining a higher $pCO_2$ may be all that is needed to improve outcomes in carbon monoxide poisoning.

Venous blood returns to the heart from the muscles and organs partially depleted of oxygen and containing a full complement of carbon dioxide. Blood from various parts of the body is mixed in the heart (mixed venous blood) and pumped into the lungs via the pulmonary artery. In the lungs, the blood vessels break up into a net of small capillary vessels surrounding tiny lung sacs (alveoli). The vessels surrounding the alveoli provide a large surface area for the exchange of gases by diffusion along their concentration gradients. After a breath of air is inhaled into the lungs, it dilutes the $CO_2$ that remains in the alveoli at the end of exhalation. A concentration gradient is then established between the partial pressure of $CO_2$ ($pCO_2$) in the mixed venous blood (pv $CO_2$) arriving at the alveoli and the alveolar $pCO_2$. The $CO_2$ diffuses into the alveoli from the mixed venous blood from the beginning of inspiration (at which time the concentration gradient for $CO_2$ is established) until equilibrium is reached between the $pCO_2$ in blood from the pulmonary artery and the $pCO_2$ in the alveoli at some time during breath. The blood then returns to the heart via the pulmonary veins and is pumped into the arterial system by the left ventricle of the heart. The $pCO_2$ in the arterial blood, termed arterial $pCO_2$ (pA $CO_2$), is then the same as was in equilibrium with the alveoli. When the subject exhales, the end of his exhalation is considered to have come from the alveoli and thus reflects the equilibrium $CO_2$ concentration between the capillaries and the alveoli. The $pCO_2$ in this gas is the end-tidal (i.e., end of an exhaled breath) $pCO_2$ (pET $CO_2$). The arterial blood also has a $pCO_2$ equal to the $pCO_2$ at equilibrium between the capillaries and alveoli.

Figure 2:
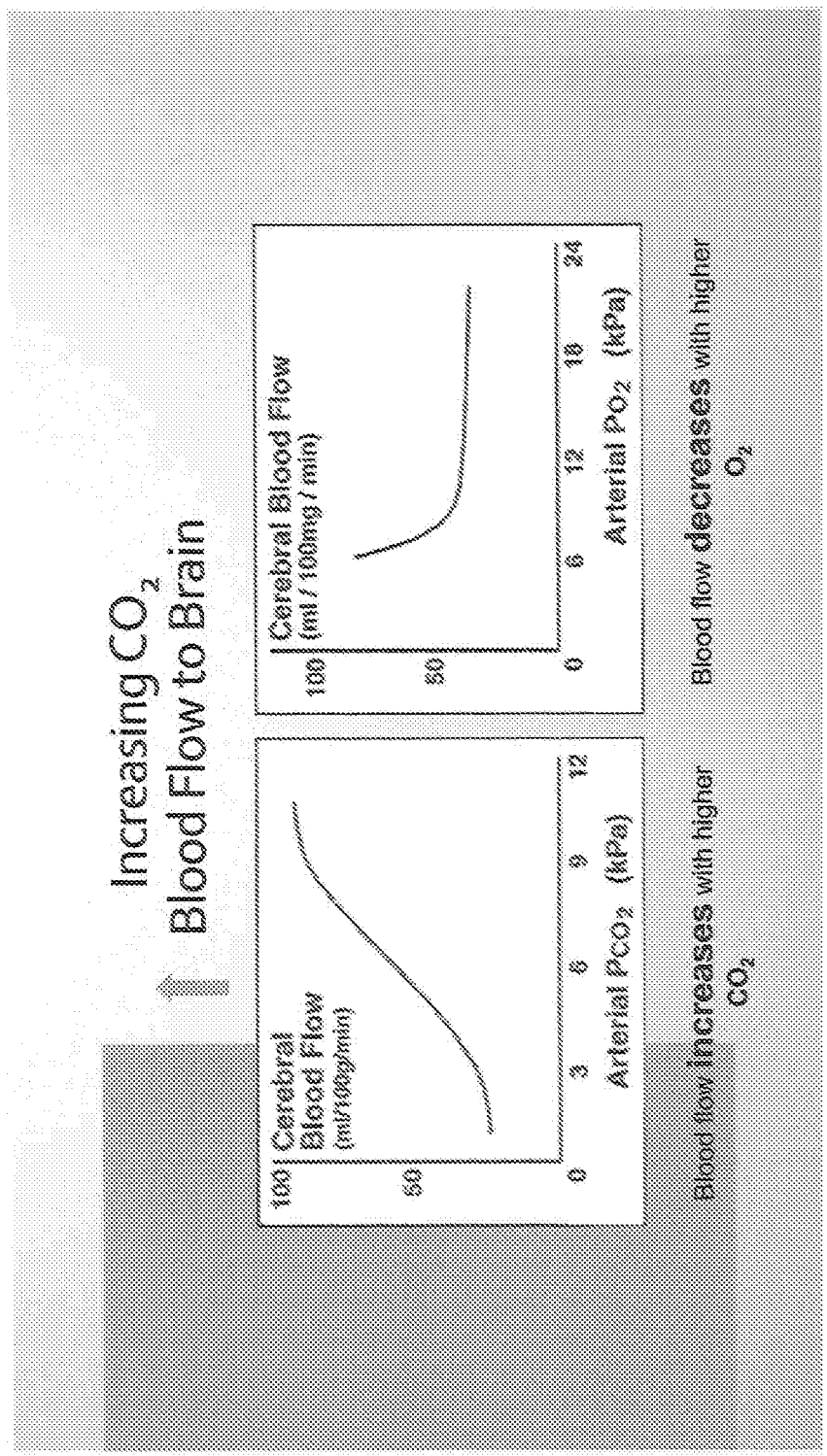
FIG. 2 are two graphs illustrating the effects on blood flow as a function of $CO_2$ and $O_2$ content of the subject's blood.

With each exhaled breath some $CO_2$ is eliminated and with each inhalation, fresh air containing minimal $CO_2$ (presently 0.04%) is inhaled and dilutes the residual equilibrated alveolar $pCO_2$, establishing a new gradient for $CO_2$ to diffuse out of the mixed venous blood into the alveoli. The rate of breathing, or ventilation (VE), usually expressed in L/min, is exactly that required to eliminate the $CO_2$ brought to the lungs and establish an equilibrium pET-$CO_2$ and pA $CO_2$ of approximately 40 mmHg (in normal humans). When one produces more $CO_2$ (e.g. as a result of fever or exercise), more $CO_2$ is carried to the lungs and one then has to breathe harder to wash out the extra $CO_2$ from the alveoli, and thus maintain the same equilibrium pA $CO_2$, but if the $CO_2$ production stays normal, and one hyperventilates, then excess $CO_2$ is washed out of the alveoli and the pA $CO_2$ falls. There are many scenarios in which it is beneficial for the inspired $CO_2$ to be greater than that which would normally come about physiologically. This heightened state of $CO_2$ in the system has many protective benefits but certainly one would not want to allow the increase in $CO_2$ to rise to dangerous levels. For instance, increases in $CO_2$ is known to increase cerebral blood flow, whereas increases in $O_2$ content decreases cerebral blood flow, as reflected in the graphs of FIG. 2. In certain clinical studies, it was found that the cerebral vessels constrict upon inhalation of 85-100% oxygen. Conversely, inhaling 5% $CO_2$ increases cerebral blood flow by 51%, and inhaling 7% $CO_2$ increases flow by 102%.

One way to contribute to the $pCO_2$ levels of the organism can be by the delivery of one or more medicaments that are known to alter pH of the organism such as carbonic anhydrase inhibitors. Some examples of carbonic anhydrase inhibitors are Topiramate, Methazolamide, Dorzolamide or Acetazolamide. Carbonic anhydrase inhibitors can act as mild diuretics by reducing NaCl and bicarbonate re-absorption in the proximal tubule of the kidney. The bicarbonaturia will thus produce a metabolic acidosis. This mild acidosis has many potential benefits in mitigating slosh as described within. Anticipated acidic pH changes that would prove beneficial would be between about 7.30 and 7.40. Associated $pCO_2$ levels would equate to $pCO_2$ levels of about 45 to 60 mmHg.

Another embodiment of elevating $pCO_2$ in the body of an organism can be a breathing circuit that maintains an elevated $pCO_2$. A circuit can maintain an estimated yet elevated end tidal $pCO_2$ by interposing one or more channels or tubes through which the individual breathes that causes a re-breathing of their previous inhaled or exhaled breath. These channels allow a mixing of inhaled ambient gas and exhaled alveolar gas. The optimal amount of gas re-breathed can be determined by estimating the individual's weight in kilograms and multiplying it by a factor, such as 7, to arrive at an estimated tidal volume in $cm^3$. In one embodiment a third of this volume can be added to the breathing circuit as dead space. This volume determines the predicted level of end tidal $CO_2$ to which the device will equilibrate. In one specific approach, the dead space volume is calibrated to approximately 10 to 50% of the tidal volume of the subject. Alternatively a secondary source of $CO_2$ could be interposed to rapidly, and on demand, increase the percentage of inspired $CO_2$. Several paper or thin walled tubes or channels can extend away from the enclosed mouth and nose portion of the device and/or several regions can be placed sequentially along the channels or tubing as perforations or weakening points so as the individual will be able to tear, cut, or break off a predetermined amount of the tubing and thus precisely alter the remaining dead space of the circuit. Demarcations and identifiers placed along the channels/tubing can help the individual decide at which perforation or weakened zone to tear, cut, or remove.

Again, these can be determined as follows: Tidal volume can be estimated by measuring one's weight in kilograms and multiplying by 7, the result would be in $cm^3$ of tidal volume. To determine the amount of dead space to add to the outflow tract of the mask, one need only take the resultant tidal volume and add a corresponding percentage of the tidal volume, such as 1-0-50%, to the outflow tract of the mask. Each incremental increase in dead space added to the outflow tract would cause an incremental increase in final $pCO_2$. For example, if the weight of the individual is 90 kg then the estimated tidal volume would be 630 $cm^3$. For a specific level of hypercapnia, the individual should re-breathe a portion of that tidal volume equal to 10-50% of the estimated tidal volume. In a specific example, the desired percentage is 45% of the tidal volume, so the dead space volume is calculated to be 290 $cm^3$. This added volume of dead space would be expected to increase the $pCO_2$ by approximately 2-3 mmHg.

In addition to the adjustable dead space, monitoring the end tidal $CO_2$ and driving an export valve to open or close to alter the source of the next inspired breath may be utilized in settings whereby precise knowledge of end tidal $CO_2$ may be required. For example if an end tidal $CO_2$ desired range is 45 mmHg, then upon noting the end tidal $CO_2$ being only 35 mmHg, the valve would be directed to close requiring the individual to take the next breath from the adjustable dead space reservoir/tubing that a previous breath had been collected into. This expiration typically has 4-5% $CO_2$ within it allowing a greater inspired $CO_2$ on the next breath. A reservoir can act as a buffer to store extra $CO_2$ gas. Even when ventilation increases, the subject breaths the accumulated elevated $CO_2$ gas allowing $pCO_2$ to rise to the desired level. A circuit to maintain normal $CO_2$ can include a non-rebreathing valve, a source of fresh gas, a fresh gas reservoir and a source of gas to be inhaled, such as from the increased dead space region or a reservoir of higher concentration of $CO_2$.

The method of controlling $pCO_2$ in a patient at a predetermined desired level can be provided comprising a breathing circuit/mask which is capable of increasing the $CO_2$ to enable an increase in cerebral blood flow and resultant cerebral blood pressure and volume. With increased cerebral blood flow, increased cerebral blood velocity, and increased intracranial pressure and volume there remains less space for intracranial tissues to move in relation to each other, thus brain pulsitility and slosh is diminished. This would require minimizing compressibility at air/fluid/tissue junctures. Although brain tissue is thought to be incompressible and fluid/blood is also relatively incompressible, the fluids are able to escape through the vessels and allow to and fro movement within the cranium and thus absorption of blast wave energies or allowance of orthostatic hypotension. If either the elevated $CO_2$ has been triggered with a resultant increase in cerebral blood flow and/or there has been increased intracranial pressure by any means before a traumatic event, the brain and its components would be less prone to slosh around within the cranium and in relation to each individual component (thus better approximating elastic collisions). This is not unlike seat-belting a passenger inside an automobile. Further, if TBI were to occur despite the above restraining effects of the increased cerebral blood flow, an elevated $CO_2$ would even serve to optimize the healing environment of the brain tissue itself by reducing the systemic inflammatory response and maximizing flow of oxygen rich hemoglobin which is more capable of delivering its oxygen due to high levels of $CO_2$ through maximizing the oxy-hemoglobin dissociation curve. Also, if an intracranial bleed were to occur despite the above protective events, the resultant blood would be constrained to the vascular tree as most, if not all, of the compensatory volume will have been "filled up" by the engorged vessels, thus reducing the degree of extravasated blood.

The benefits of the rebreathing methods and apparatuses disclosed herein typically begin to accrue after the second inhalation of the air with the $CO_2$ content elevated as described. The benefits continue as long as the person is rebreathing the expired $CO_2$. The benefits continue for a limited duration after the rebreathing has ceased and the person is breathing normally, since the $pCO_2$ in the blood stream takes some time to regulate. Volume changes in the cranium may persist for hours as the elevated $pCO_2$ opens the blood brain barrier (BBB) to sugar movement, and fluids and water follow the sugar gradient. When the $CO_2$ comes back down, the BBB closes and traps the extra sugar (with its water) within the cranium for a prolonged period of time (hours). However, as long as the $pCO_2$ of the blood stream is above normal, the person still experiences the $CO_2$ driven beneficial effect of the increased partial pressure. It is contemplated that in certain situations, such as where the rebreathing method disclosed herein is used to drive respiration, the duration of the benefit may be shorter-lived—as one stops the added $CO_2$, the benefits cease within seconds.

Figure 3:
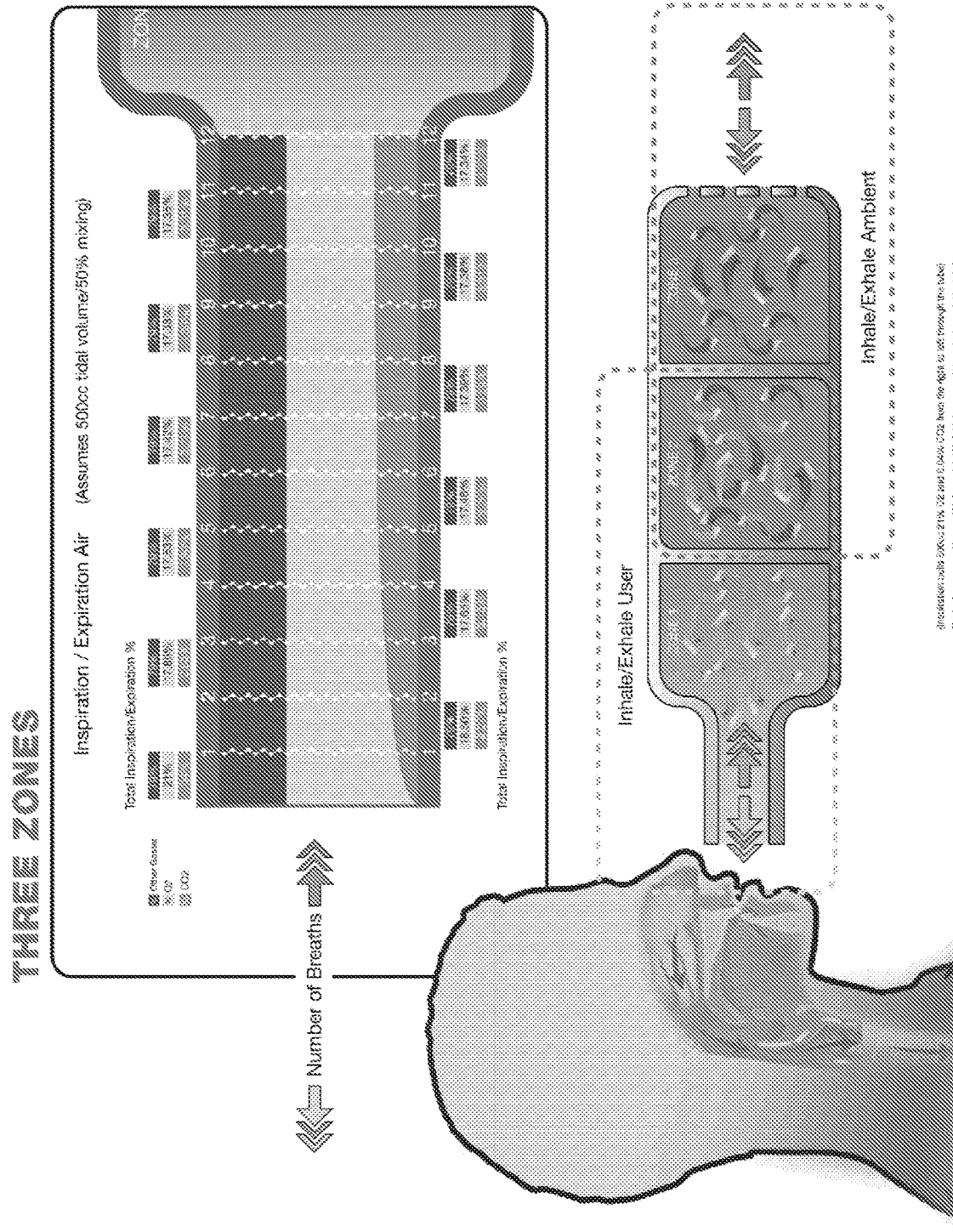
FIG. 3 is a chart showing the composition of air during inhale and exhale and three zones of inspiration and exhalation air.

The present disclosure contemplates a portable breathing apparatus worn by a person that increases the $CO_2$ inhalation to increase cerebral and spinal blood flow and volume, mitigate the effects of TBI, orthostasis, or assist in driving respiration. In normal inspiration, the person pulls in 500 cc of air, with 21% $O_2$ and 0.04% $CO_2$. In normal expiration, the person pushes 500 cc of air (tidal volume TD), which includes 16% $O_2$ and 4.5% $CO_2$. The present disclosure contemplates a device that controls the mixture of the air that is inhaled by controlling the air that is exhaled. As illustrated in FIG. 3, the device effectively creates three zones of inspiration and expiration of air within an enclosed extended volume. In the first zone nearest the mouthpiece, the $O_2/CO_2$ mixture is primarily oxygen, while in the third zone at the outlet of the enclosed volume the mixture is primarily $CO_2$. The first two zones, Zones 1 and 2, represent the volume of air that is inhaled and exhaled by the user. The last two zones, Zones 2 and 3, represent the volume of air that is fed by ambient air surrounding the device. The middle zone, Zone 2, is the dead space that overlaps the user and the ambient volumes of air. Increasing this intermediate zone increases the $CO_2$ content of the air that is inhaled by the user by, in effect, creating a dead zone for the $CO_2$ exhaled by the user. The $CO_2$ in this dead zone, Zone 2, includes the normal 0.04% $CO_2$ found in the ambient air, with the 3.3% $CO_2$ typically exhaled by the user. As reflected in the chart in FIG. 3, the content of other gases in the inhaled/exhaled air does not change. Instead, the ratio of $O_2$ to $CO_2$ changes along the mouthpiece. Creating and controlling the dead space Zone 2 changes the $O_2/CO_2$ ratio by increasing the amount of $CO_2$ retained within the dead space, which replaces the volume of $O_2$ that would ordinarily be inhaled with each breath.

Figure 4:
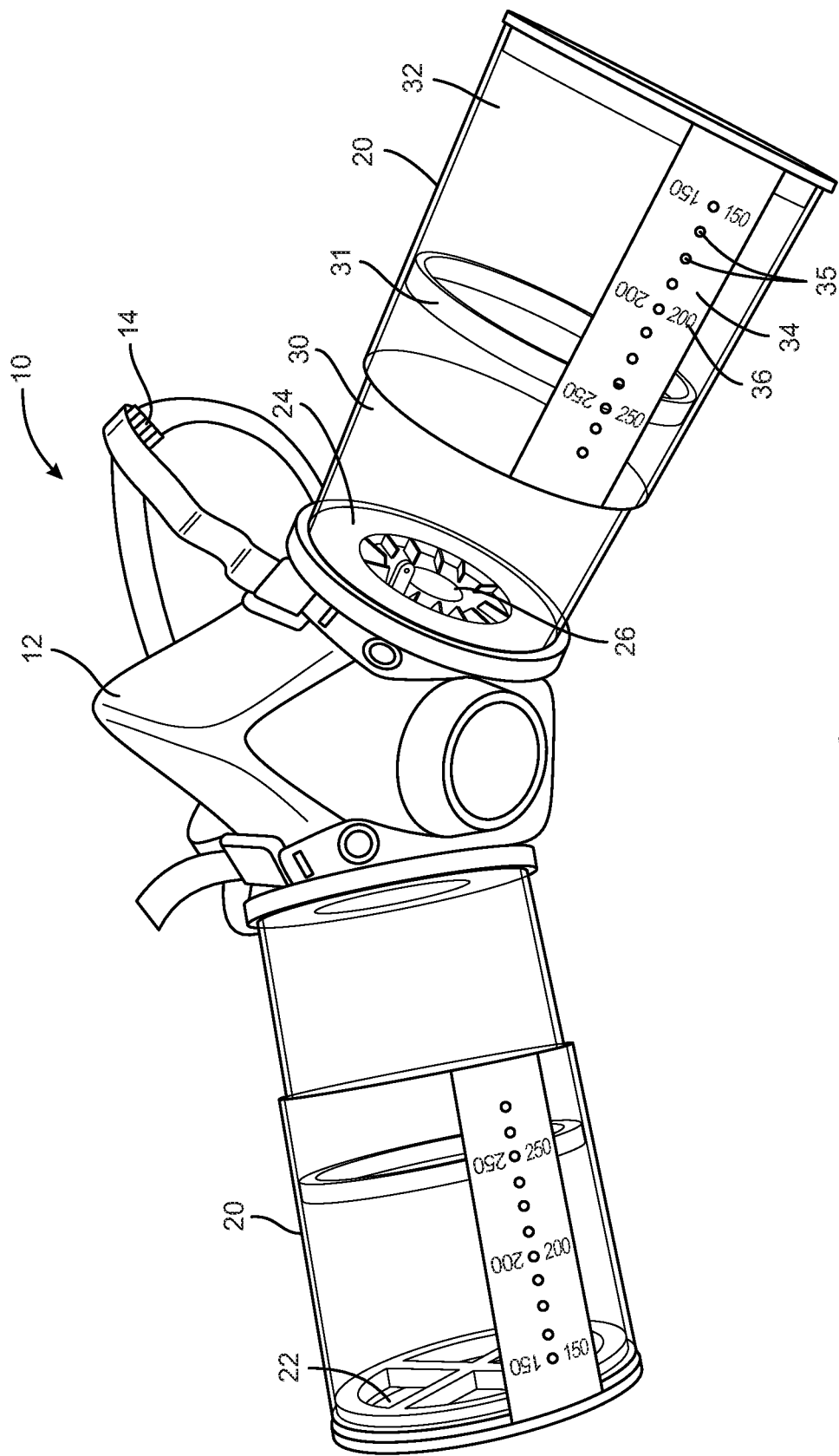
FIG. 4 is a perspective view of a breathing apparatus according to one embodiment of the present disclosure.
Figure 5:
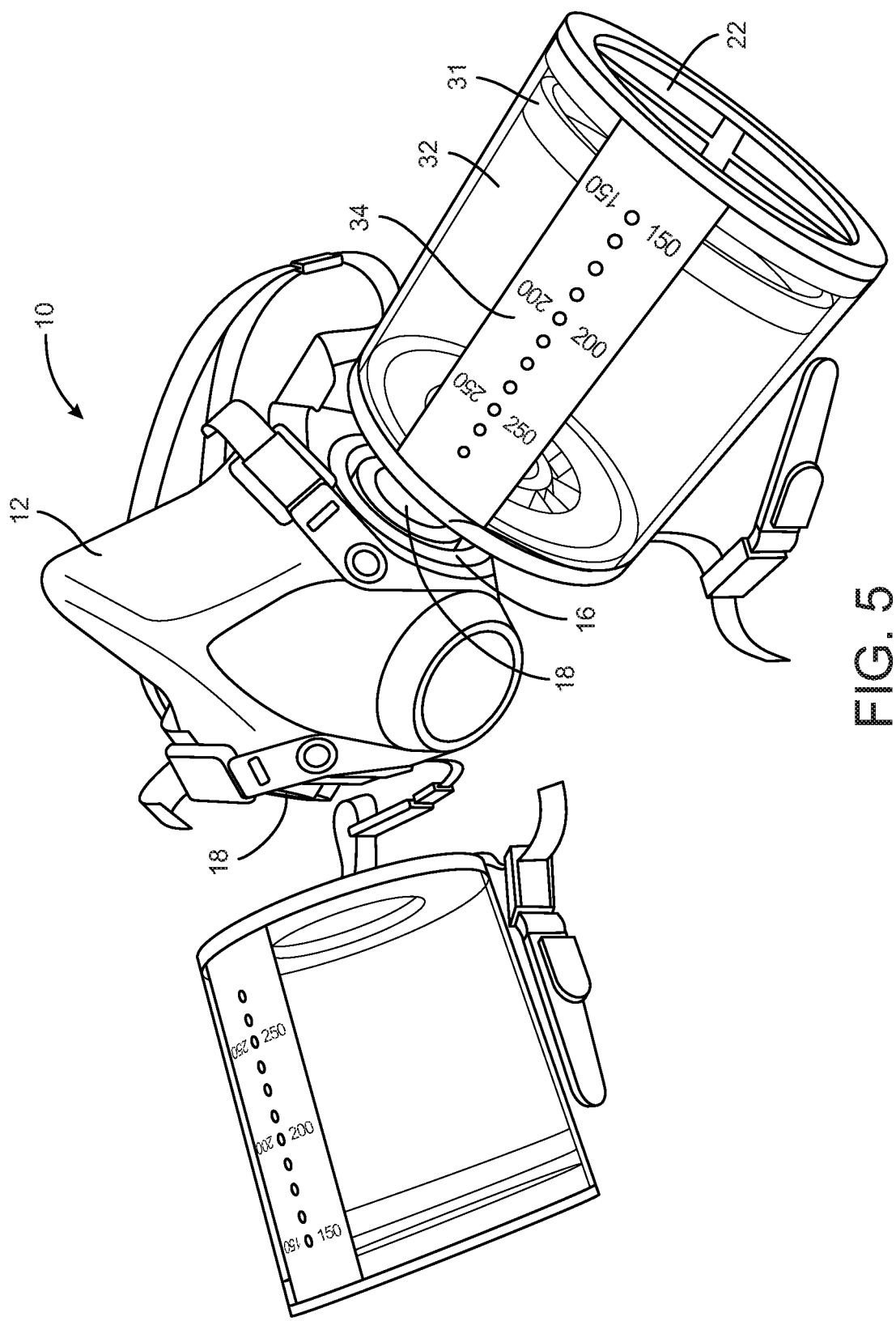
FIG. 5 is a perspective view of the apparatus in FIG. 4 shown with the telescoping chambers removed.

One embodiment of a breathing apparatus 10 is shown in FIGS. 4-5. The apparatus 10 includes a face mask 12 that is sized and configured to cover the user's mouth and nose. A strap arrangement 14 is provided to support the mask portion on the user's head. By way of example, the face mask and strap arrangement can be configured similar to a conventional pilot's oxygen mask. However, in lieu of the diluter valve of the conventional oxygen mask, the apparatus 10 includes a pair of fittings 18 for mounting a pair of exhale chambers 20. Each chamber includes a mounting fitting 24 for engagement with a corresponding fitting 18 of the face mask 12. The mounting fitting includes a central opening 26 for communication with the opening 16 of the face mask. Each chamber 20 includes an outlet opening 22 at the distal end of the chamber that is in communication with the ambient air.

Figure 6:
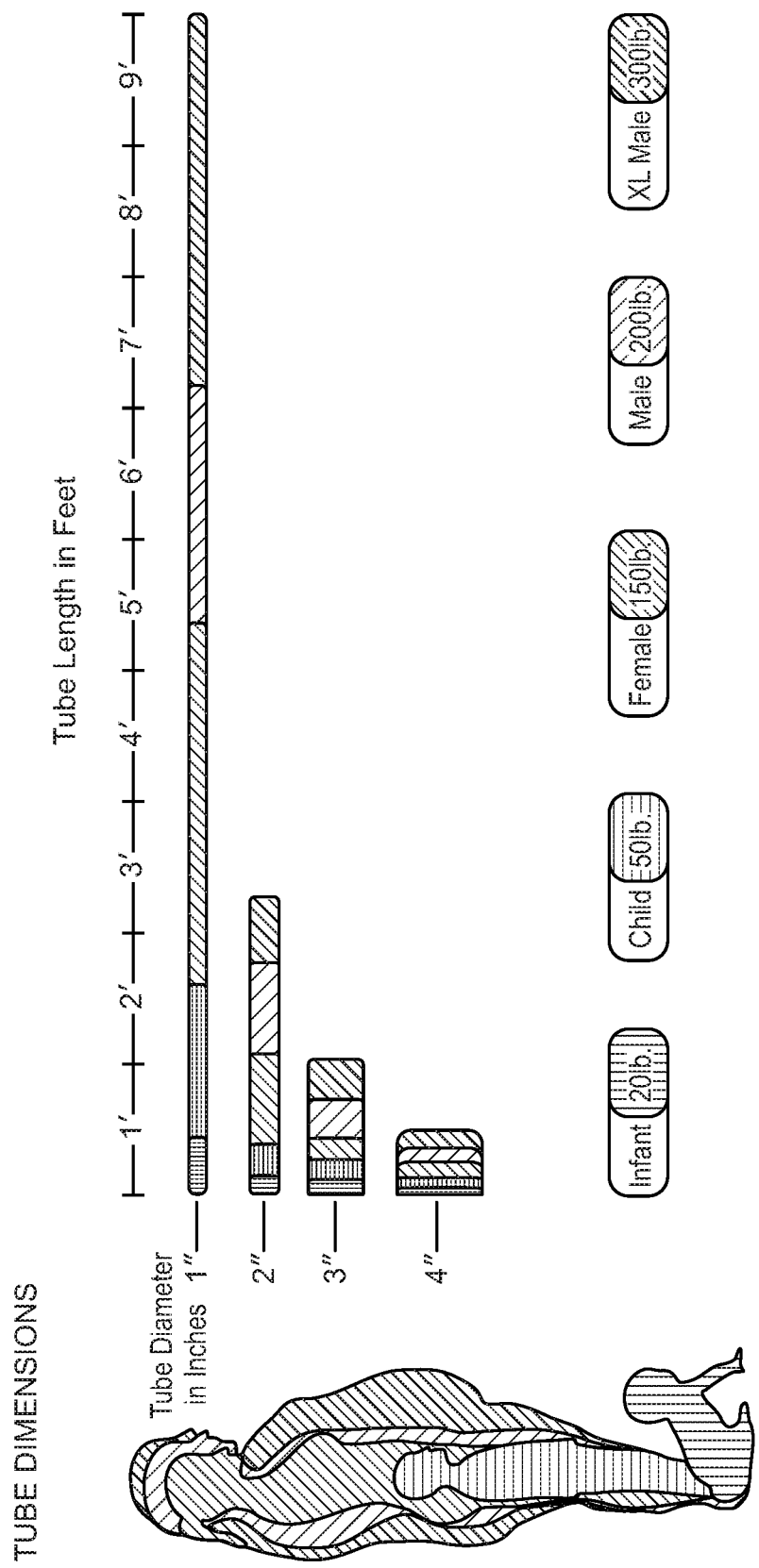
FIG. 6 is a chart of dead space tube dimensions as a function of the weight of the subject.

The chamber 20 provides the dead space Zone 2 (FIG. 3) discussed above so that a certain amount of exhaled $CO_2$ is mixed with ambient air drawn in through the opening 22 to increase the $CO_2$ content of the air inhaled by the user. In one feature of the present disclosure, the dead space volume is calibrated to the physiological characteristics of the user. In one aspect, the dead space volume is calibrated to the body weight of the individual. In particular the desirable dead space volume increases with the weight of the individual, as summarized in the chart of FIG. 6. For a particular diameter of the chamber (i.e., tube diameter), the length of the chamber (tube) increases with the weight of the user, which means that the overall volume of the dead space increases. For example, a breathing apparatus 10 having a chamber diameter of 1 inch, the length of the chamber need only be ½ foot (6 inches) for an infant, with a volume of about 4.7 $in^3$ (77 cc). For a 300 lb. user, the 1 inch diameter chamber needs to be about 8 inches long, for a volume of about 75.4 $in^3$ (1236 cc). It can be appreciated that the chamber length can be shortened by increasing the diameter of the chamber, as reflected in the significant decrease in length for a 3 or 4 inch diameter chamber.

For the embodiment shown in FIGS. 4-5, the chamber 20 is adjustable to change the dead space volume. Thus, the chamber 20 includes two telescoping chamber portions 30, 32. The interior chamber portion 30 includes a ring 31 at its distal end that serves as a sliding gasket that permits relative movement of the two portions while exerting sufficient friction to hold the two portions in a desired relationship. In addition, the ring 31 serves as a volume indicator with respect to the volume scale 34 disposed on the outer chamber portion 32. In the illustrated embodiment, the scale 34 includes a plurality of evenly spaced windows 35 that correspond to fixed volumetric increments, such as 10 cc increments. The scale can also include numeric indicia 36 identifying certain volumes, such as 150, 200 and 250 cc. The ring 31 can be in a high contrast color that is visible through the windows 35 or indicia 36 to provide a clear visual indication of the volume setting for the telescoping chamber portions 30 of the apparatus 10.

Figure 7A:
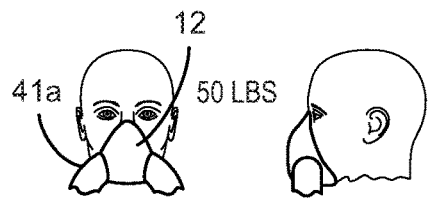
FIGS. 7A-7C are depictions of a face-mask type breathing apparatus according to the present disclosure.
Figure 7B:
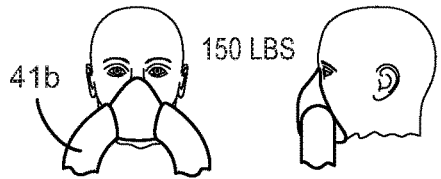
Figure 7C:
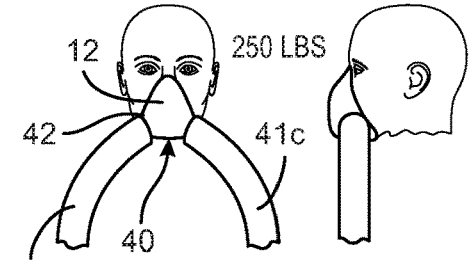

In an alternative embodiment, the telescoping chamber 20 can be replaced by a series of elongated hollow tubes, as depicted in breathing apparatus 40 shown in FIG. 7. The face mask 12 can be as shown in FIG. 4, in particular including the fitting 16. A series of increasingly longer tubes 41a, 41b and 41c can each include a fitting 42 configured to engage the face mask fitting 16 to that the tubes can be optionally engaged to the face mask. The tubes have a generally fixed diameter and a length calibrated to the weight of the user, as reflected in the chart of FIG. 6. It can be appreciated that the tube 41a for a 50 lb. person is much shorter than the tube 41c for a 250 lb. person. As with the telescoping chamber of the apparatus 10, the selection of tubes calibrates the dead space volume to the weight of the user to achieve an optimum $CO_2$ volume being inhaled by the user.

Figure 8A:
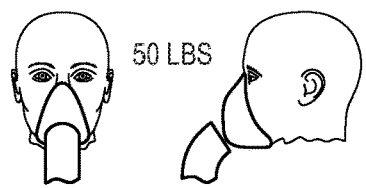
FIGS. 8A-8C are depictions of an alternative face-mask type breathing apparatus according to the present disclosure.
Figure 8B:
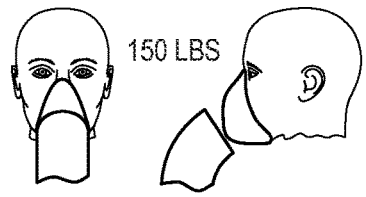
Figure 8C:
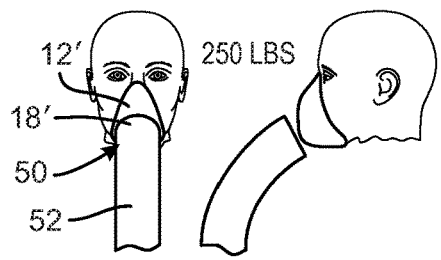

In a modification of the apparatus 40, the two tubes can be replaced by a single tube with a larger diameter, as in the apparatus 50 shown in FIG. 8. The face mask 12' is modified from the face mask 12 described above in that a single fitting 18' is provided to engage the single tube 52. In order to provide the same dead space volume as the two-tube version of FIG. 7, the single tube version requires a larger diameter tube in order to maintain the maximum length of the tube 52 to a manageable length. In this embodiment, the single tube 52 may have a diameter of 4 inches, with the lengths adjusted according to the weight of the user, as shown in FIGS. 8(a), 8(b) and 8(c). It can be appreciated that the principle of operation of the two-tube and the single tube versions are the same—the apparatus provides a calibrated dead space volume where exhaled $CO_2$ combines with $CO_2$ inhaled from ambient air to increase the $pCO_2$ of the user to achieve the benefits and outcomes described above.

Figure 9A:
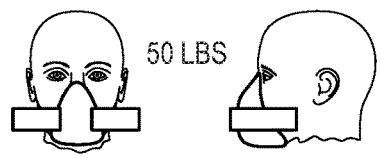
FIGS. 9A-9C are depictions of another face-mask type breathing apparatus according to the present disclosure.
Figure 9B:
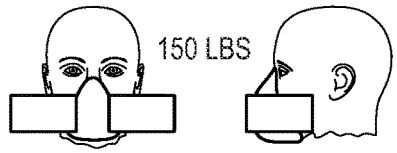
Figure 9C:
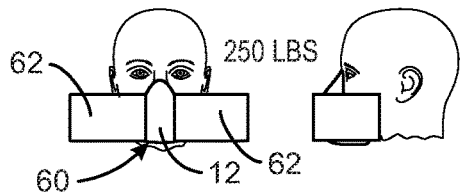

In a further modification of the apparatus 40, the tubes of a two-tube version 60 can be modified as shown in FIG. 9. In this version, the tubes 62 can be curved laterally adjacent the cheek of the user. The tubes 62 can also be generally rectangular in cross-section, rather than circular, but with a cross-sectional area equivalent to the tubes 41c. A series of differently sized tubes 62 can be provided in different lengths to adjust the dead space volume as discussed above.

Figure 10:
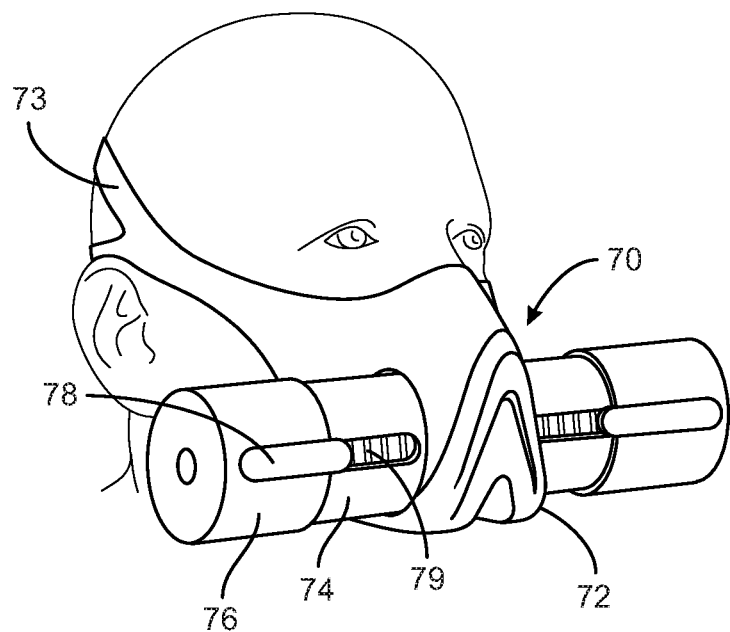
FIG. 10 is a depiction of a face-mask type breathing apparatus having an adjustable dead space volume according to the present disclosure.

Returning to the adjustable embodiment of FIGS. 4-5, other breathing apparatus are contemplated with similar provisions for adjusting the dead space volume of the apparatus. The breathing apparatus 70 of FIG. 10 includes a face mask 72 that can include an integral strap arrangement 73. The mask also includes fixed tubes 74 at opposite sides of the mask that receive telescoping tubes 76. A latch 78 and ratchet 79 arrangement can be provided between the fixed and telescoping tubes 74, 76 that permits adjustment of the overall length of the dead space, and thus the dead space volume.

Figure 11:
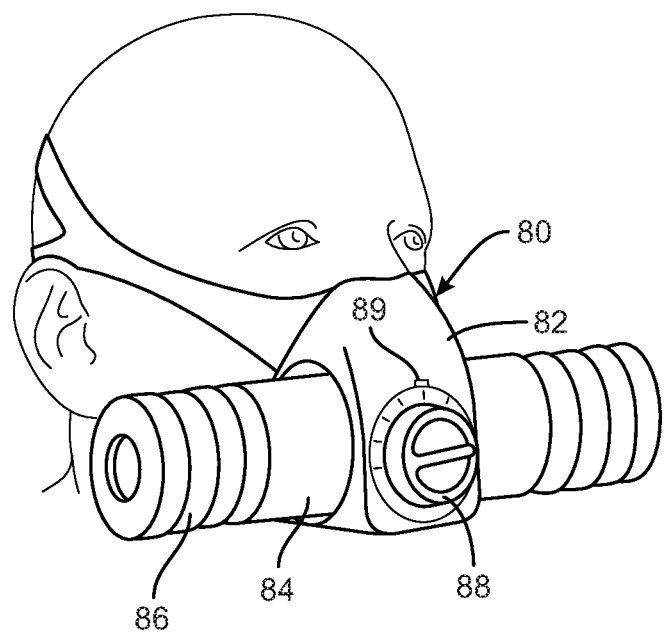
FIG. 11 is a depiction of a face-mask type breathing apparatus having an adjustable dead space volume according to the present disclosure.

The breathing apparatus 80 shown in FIG. 11 includes a similar face mask 82 with fixed tubes 84. However, in this embodiment, the adjustable tubes 86 are accordion-type tubes that can be compressed or extended. An adjustment dial 88 is connected to an adjustment mechanism fastened to the distal ends of the adjustable tubes 86 so that rotation of the dial extends or retracts the accordion-type tubes. The face mask 82 may include indicia around the dial 88 corresponding to the dead space volume for particular degree of extension of the accordion-type tubes 86.

Figure 12:
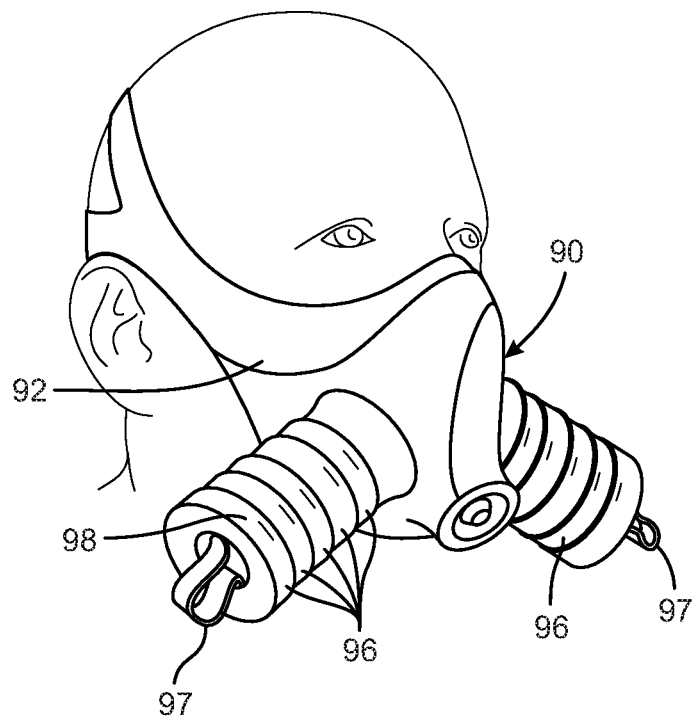
FIG. 12 is a depiction of an alternative face-mask type breathing apparatus having an adjustable dead space volume according to the present disclosure.

In a related concept, a breathing apparatus 90 shown in FIG. 12 includes a series of nested tubular sections 96 that can be extended by pulling on a strap 97 and retracted by pushing the sections toward the face mask 92. Each tubular section 96 can include indicia corresponding to the dead space volume so that as each successive tubular section is exposed the volume indicia increases.

Figure 13:
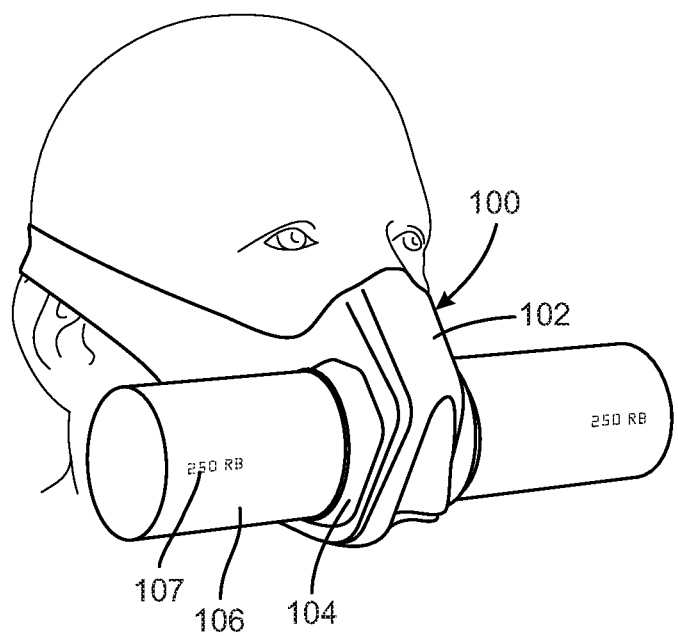
FIG. 13 is a depiction of a face-mask type breathing apparatus having a replaceable dead space volume according to the present disclosure.
Figure 14:
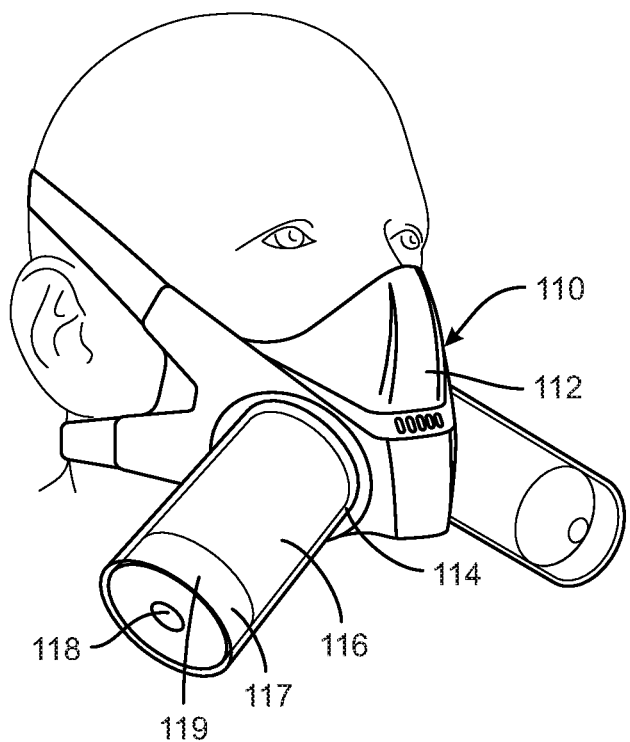
FIG. 14 is a depiction of a face-mask type breathing apparatus having a volume adjustment feature according to the present disclosure.
Figure 15:
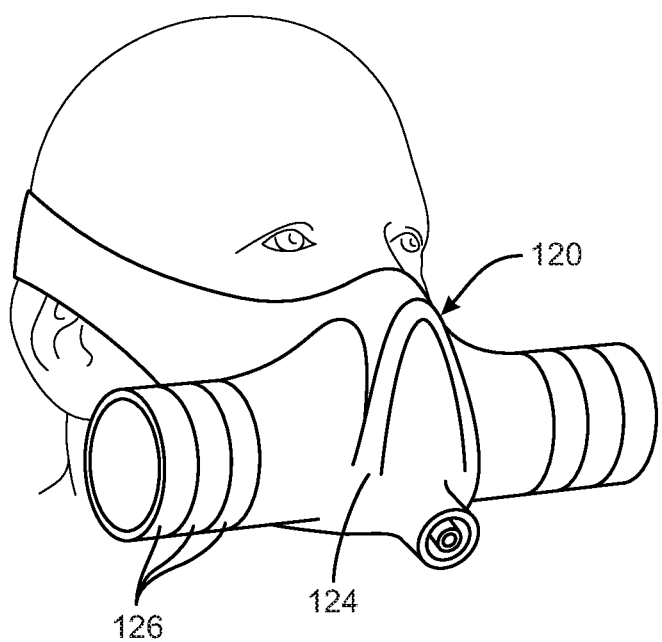
FIG. 15 is a depiction of an alternative face-mask type breathing apparatus having a replaceable dead space volume according to the present disclosure.

Breathing apparatuses with fixed volume cylinders are shown in FIGS. 13-15. The apparatus 100 includes a face mask 102 with an integral fitting 104 to receive canisters 106. The canisters can include a threaded end to engage threads within the fitting 104. The canisters 106 can have predetermined fixed volumes, as indicated by the indicia 107. The apparatus 100 thus includes a plurality of differently sized canisters 106 representing a range of dead space volumes. The appropriately sized canister can be selected based on the weight of the user.

The breathing apparatus 110 includes a face mask 112 with an integral fitting 114 adapted for engagement with a fixed volume canister 116. Although the canister 116 is removable in this embodiment, it is removed to introduce a volume spacer 117 that reduces the interior volume of the canister. The spacer 117 can be bowl-shaped with an opening 118 at the base of the spacer adjacent the interior of the canister. In effect the spacer 117 moves the inlet opening 118 to the ambient air closer to the face mask 112, thereby reducing the dead space volume within the canister. A plurality of spacers 117 with corresponding volume indicia 119 can be provided to adjust the dead space volume according to the weight of the user.

In another approach, a breathing apparatus 120 can include a plurality of volume extenders 126 that are configure to engage each other and engage the face mask 124. The extenders can encompass a common volume, such as 50 cc, so that combining multiple extenders can produce a predetermined dead space volume.

Figure 16:
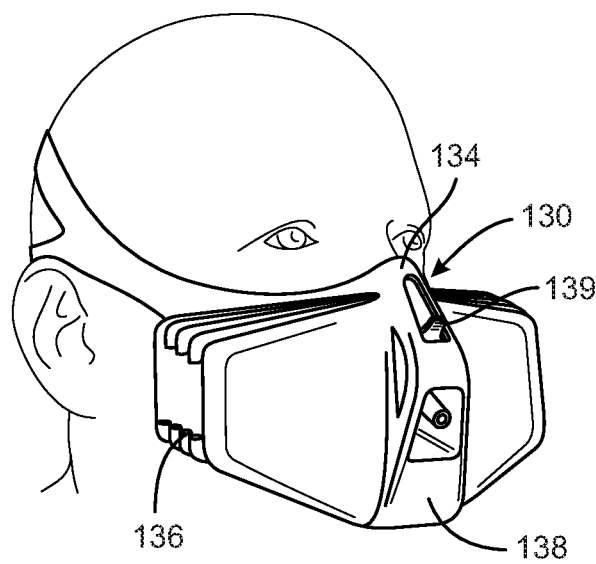
FIG. 16 is a depiction of a further alternative face-mask type breathing apparatus having an adjustable dead space volume according to the present disclosure.

The breathing apparatus 130 shown in FIG. 16 incorporates a bellows 136 within the mask 134. The bellows can be increased or decreased by manipulating an outer plate 138. A slide lever 139 on the face mask may be used to facilitate controlled expansion or compression of the bellows 136 to achieve a desired dead space volume.

Figure 17:
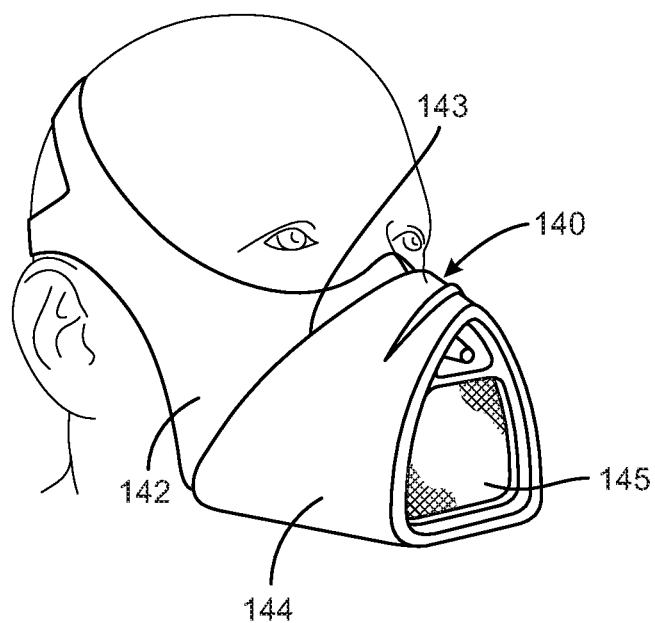
FIG. 17 is a depiction of an alternative face-mask type breathing apparatus having a replaceable dead space volume according to the present disclosure.
Figure 18:
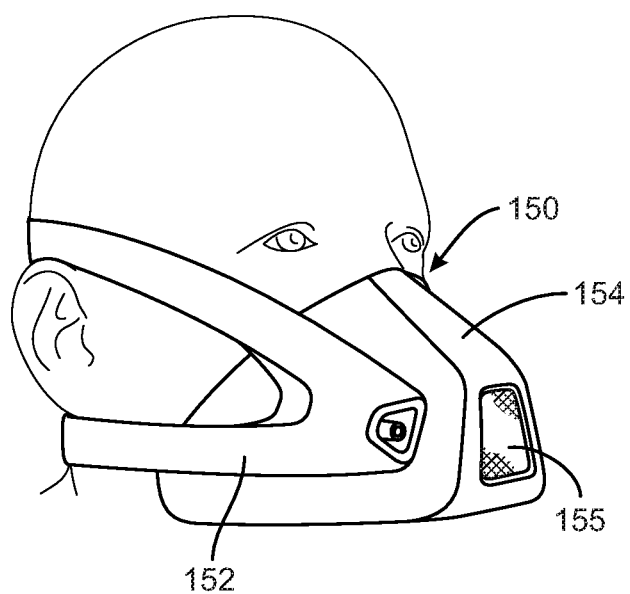
FIG. 18 is a depiction of another alternative face-mask type breathing apparatus having a replaceable dead space volume according to the present disclosure.
Figures 19A, 19B, 19C:
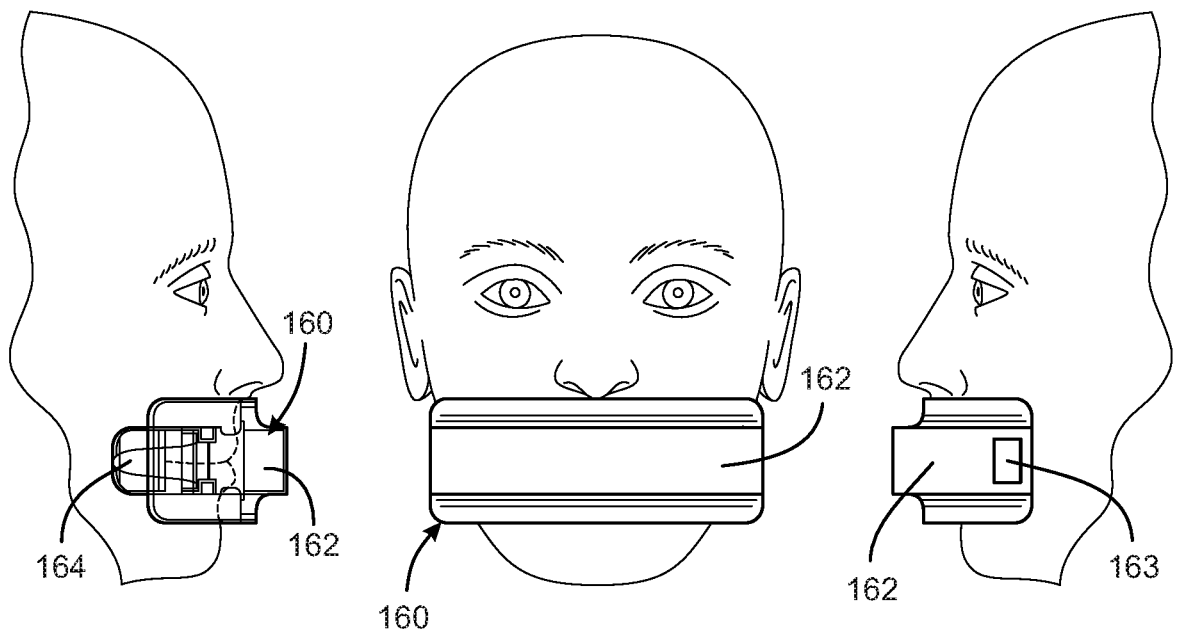
FIGS. 19A-19C are depictions of a mouthpiece-type breathing apparatus according to the present disclosure.

In another fixed volume approach, a breathing apparatus 140 shown in FIG. 17 includes a head strap 142 with a mounting 143 for removable engagement with a fixed volume chamber 144. The chamber 144 defines a predetermined dead space volume between the inlet 145 and the user's face. A plurality of differently sized chambers 144 can be provided to achieve different dead space volumes. The breathing apparatus 150 shown in FIG. 18 is similar in that a fixed volume chamber 154 is provided that defines a dead space volume between an inlet 155 and the user's face. A strap assembly 152 can be configured to engage the sides of the chamber 155 as shown in FIG. 18.

The breathing apparatuses shown in FIGS. 4-18 are particularly suited for emergency, hospital or therapy uses, in large part due to their relatively bulky nature. For instance, it is contemplated that EMTs are provided with the breathing apparatuses capable of providing dead space volumes for a wide range of patients. The EMT can administer treatment with the breathing apparatus in situations where a head injury did or may have occurred. The treatment with the breathing apparatus can continue as needed to increase the $pCO_2$ of the patient for the reasons discussed above.

Breathing apparatuses adapted for active use are also contemplated by the present disclosure. In particular, embodiments that can be gripped between the lips and/or teeth of the user are shown in FIGS. 19-25. The breathing apparatus 60 shown in FIGS. 19A-C includes a chamber 162 that is curved around the jaw of the user. A mouthpiece 164 is integral with the chamber 162 and configured to be gripped by the teeth and/or lips of the user, similar to a typical sports mouth guard. The chamber 162 includes openings 163 at the ends of the curved chamber 162. The chamber is dimensions to provide a predetermined dead space volume, as discussed above. It is contemplated that the size of the chamber and therefore the size of the apparatus 160 is varied depending on the necessary dead space volume for a particular user.

Figures 20A, 20B:
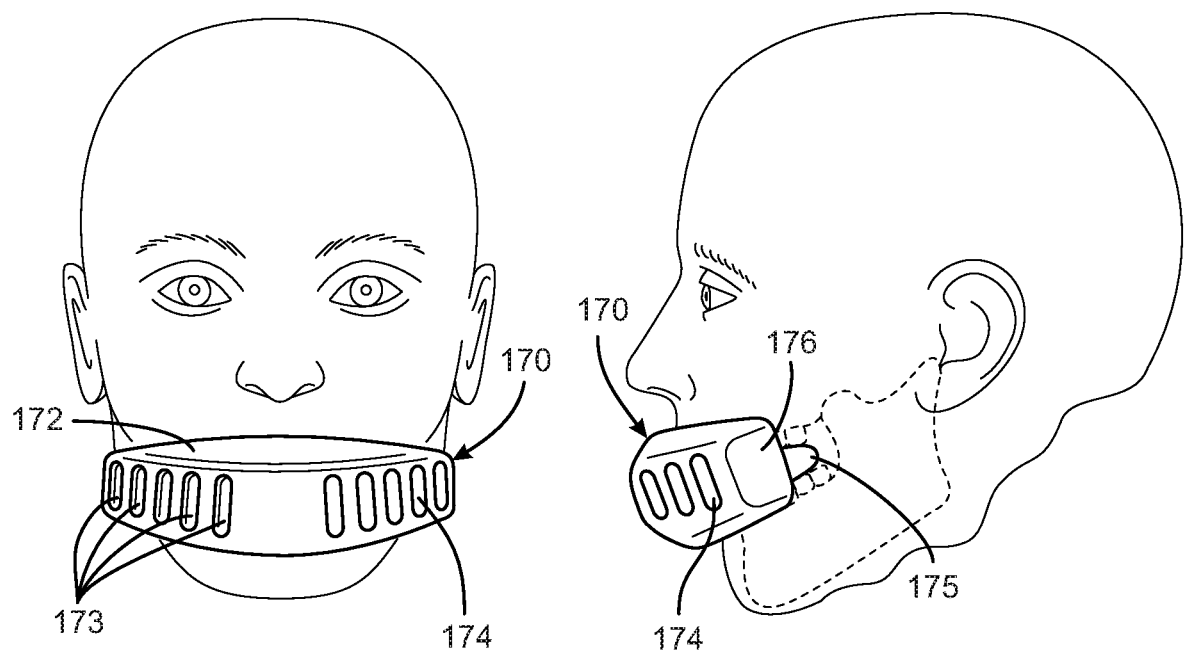
FIGS. 20A-20B are depictions of another mouthpiece-type breathing apparatus according to the present disclosure.

The breathing apparatus 170 shown in FIGS. 20A-B is similar to the apparatus 160 in that the chamber 172 includes a mouthpiece 175 and defines a fixed volume with an outlet 176 at the opposite ends of the chamber. However, in this embodiment, the internal volume within the chamber 172 can be adjusted by volume pods 174 placed within slots 173 that communicate with the internal volume. The volume pods reduce the internal volume from the maximum total volume of the chamber 172, thereby adjusting the dead space volume.

Figure 21:
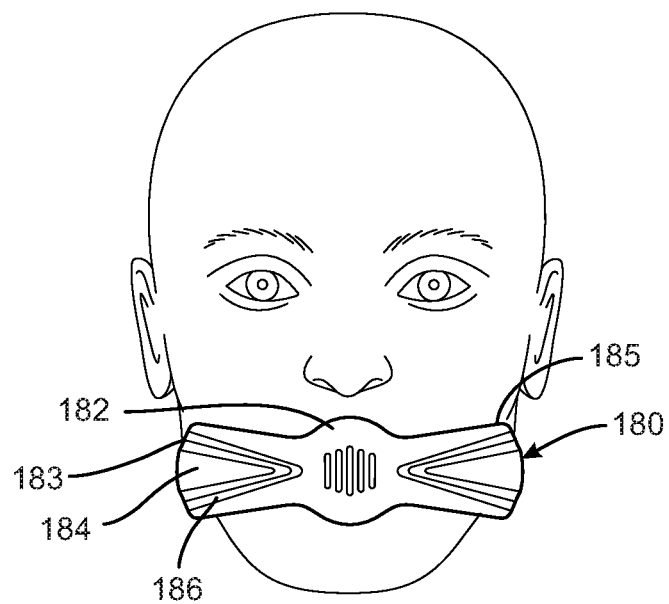
FIG. 21 is a depiction of a mouthpiece-type breathing apparatus having an adjustable dead space volume according to the present disclosure.

The breathing apparatus 180 shown in FIG. 21 includes an adjustable chamber 182 with outlets 183 at opposite ends. The chamber is defined by an inner wall 185 that includes a mouthpiece as contemplated in the previous embodiments, an outer wall 184 and a bellows structure 186 between the two walls. The bellows can be expanded or contracted to adjust the volume within the chamber 182 in a manner similar to the embodiment shown in FIG. 16.

Figure 22:
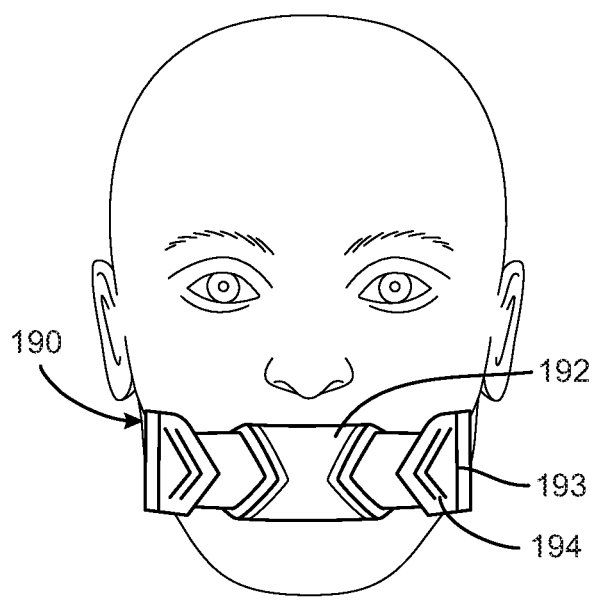
FIG. 22 is a depiction of another mouthpiece-type breathing apparatus having an adjustable dead space volume according to the present disclosure.

The breathing apparatus 190 shown in FIG. 22 includes a chamber 192 with end outlets 193. The outlets are at the ends of slidably adjustable tubes 194 that maybe configured like the tubes 76 shown in FIG. 18, like the tubular sections 96 in the embodiment of FIG. 12, or like the telescoping chamber configuration shown in FIG. 4.

Figure 23:
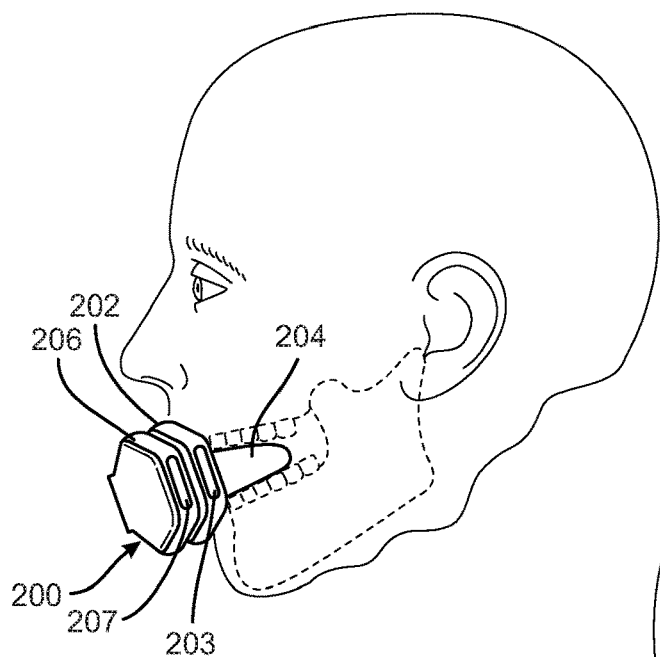
FIG. 23 is a depiction of an alternative mouthpiece-type breathing apparatus having an adjustable dead space volume according to the present disclosure.

The breathing apparatus 200 of FIG. 23 includes a base chamber 202 that incorporates the mouthpiece 204 and end outlets 203. An additional chamber 206 can be mounted onto the base chamber in a manner that permits fluid or gas communication between the chambers. In one embodiment, the two chambers can be connected with a bayonet mount, similar to the mount used on a traditional camera lens. The additional chamber includes outlets 207 at its ends. The additional chamber 206 may be configured for mounting a further chamber 207, wherein each chamber 206 includes bayonet mounts on the front and back faces of the chamber. Each chamber 203, 206 has a fixed volume, so combining the chambers can achieve a predetermined dead space volume.

Figure 24:
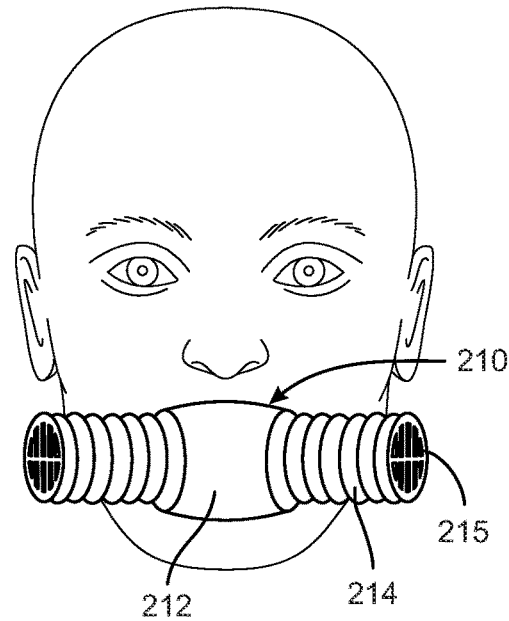
FIG. 24 is a depiction of yet another mouthpiece-type breathing apparatus having an adjustable dead space volume according to the present disclosure.

An alternative accordion-type embodiment is shown in FIG. 24. A main chamber 212 of the breathing apparatus 210 includes the mouthpiece and supports expandable accordion tubes 214, each tube including an outlet 215. As with the accordion embodiment in FIG. 11, the accordion tubes 214 can be extended or contracted to adjust the dead space volume of the apparatus 210.

Figure 25:
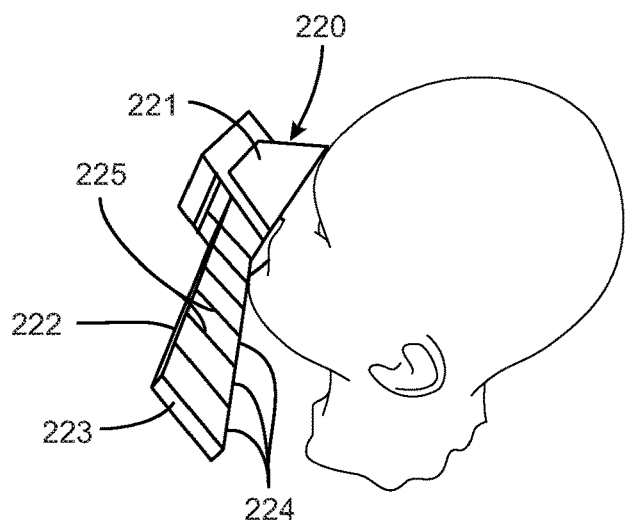
FIG. 25 is a depiction of a further mouthpiece-type breathing apparatus having an adjustable dead space volume according to the present disclosure.
Figure 26B:
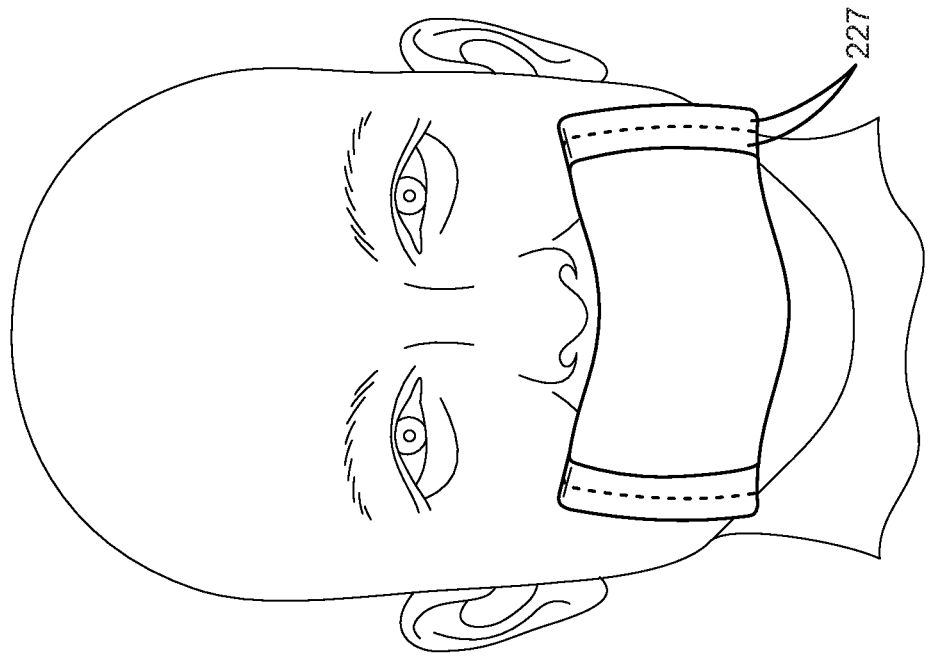
FIGS. 26A-B are depictions-of a further mouthpiece-type breathing apparatus having an adjustable dead space volume according to the present disclosure.
Figure 26A:
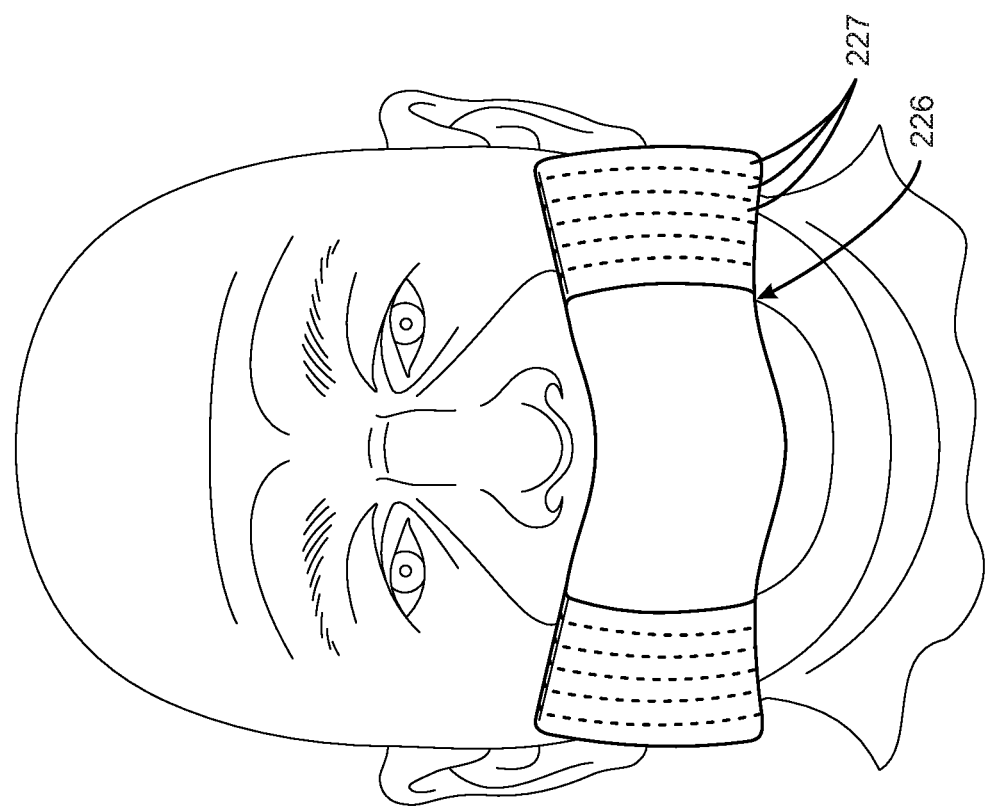
Figure 27B:
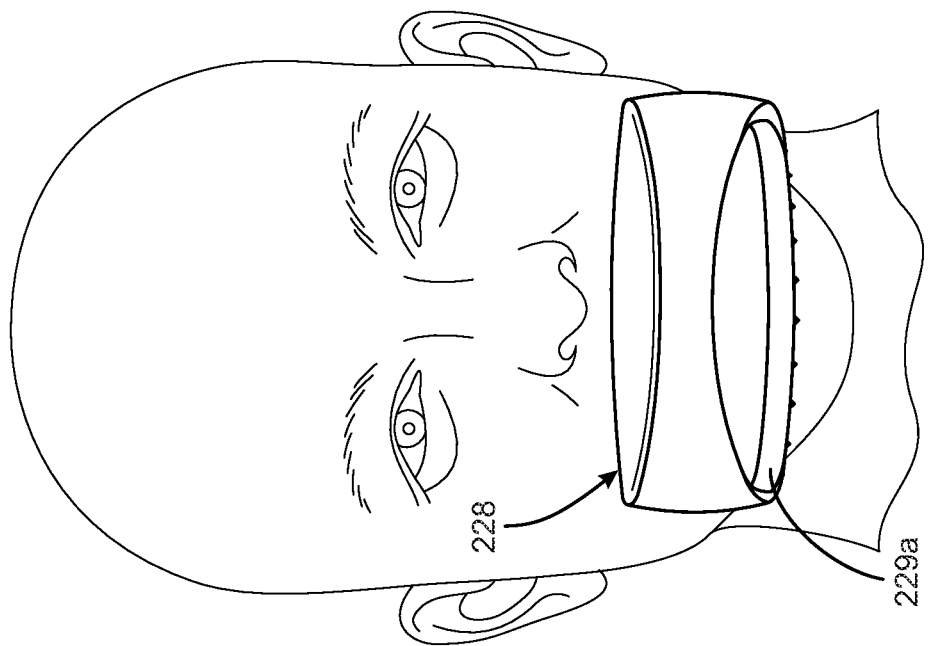
FIGS. 27A-B are depictions-of a mouthpiece-type breathing apparatus having an adjustable dead space volume according to the present disclosure.
Figure 27A:
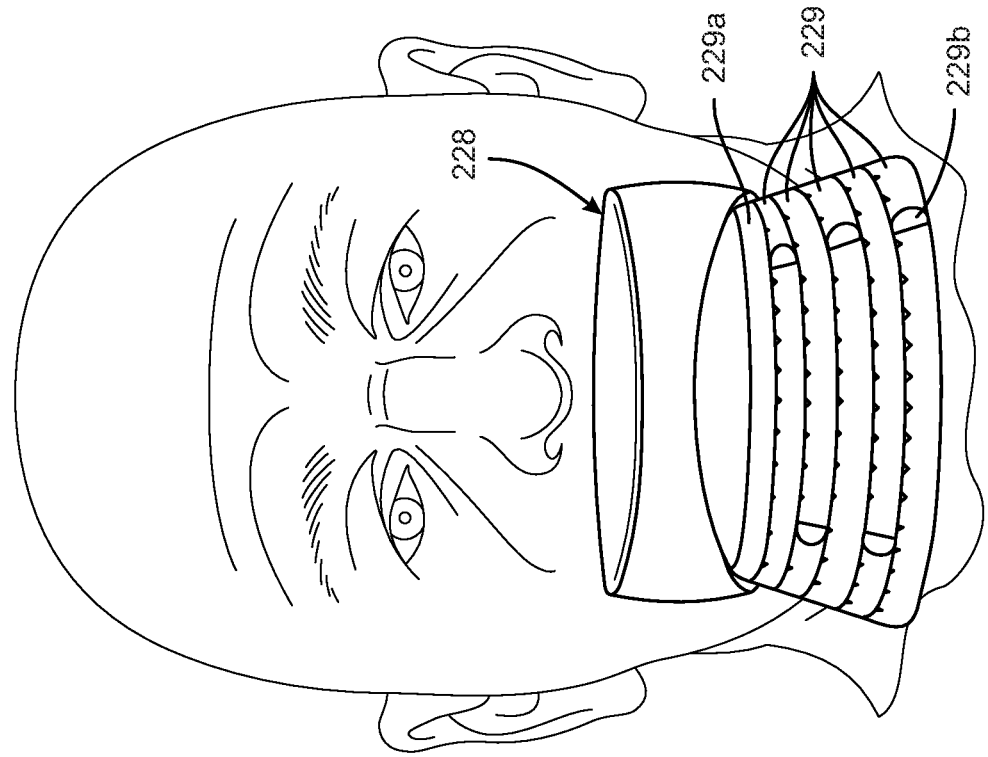
Figure 28A:
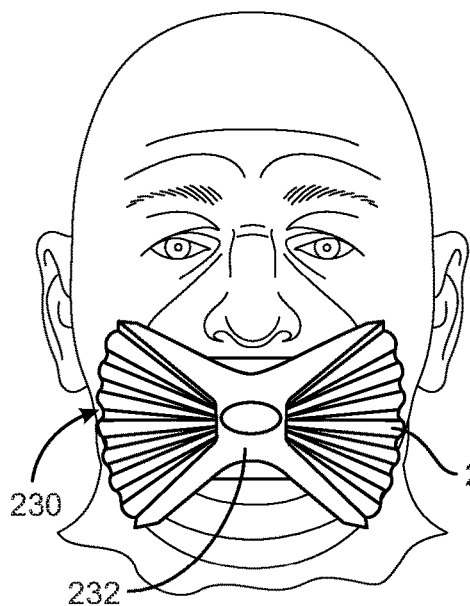
FIGS. 28A-C are depictions-of a mouthpiece-type breathing apparatus having an adjustable dead space volume according to the present disclosure.
Figure 28B:
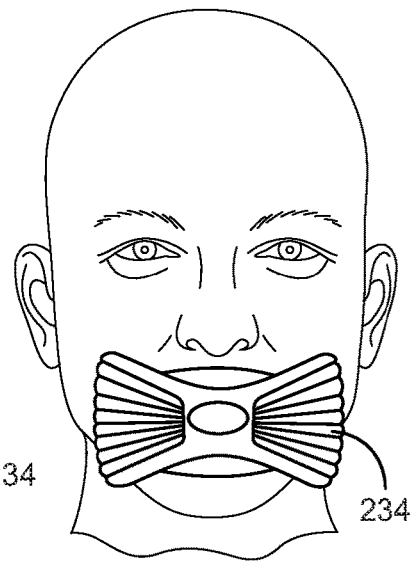
Figure 28C:
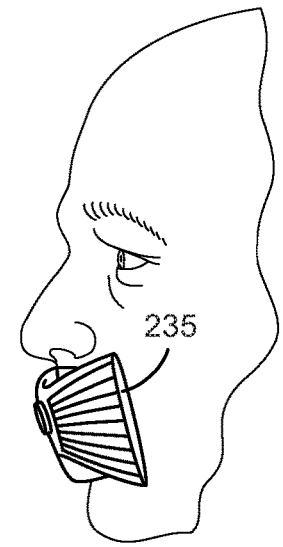
Figure 29A:
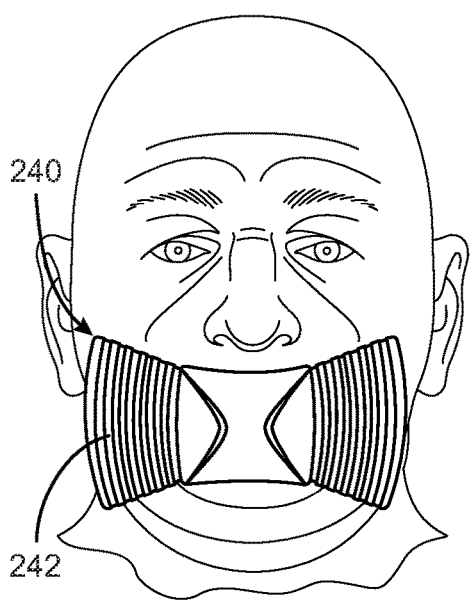
FIGS. 29A-C are depictions-of another mouthpiece-type breathing apparatus having an adjustable dead space volume according to the present disclosure.
Figure 29B:
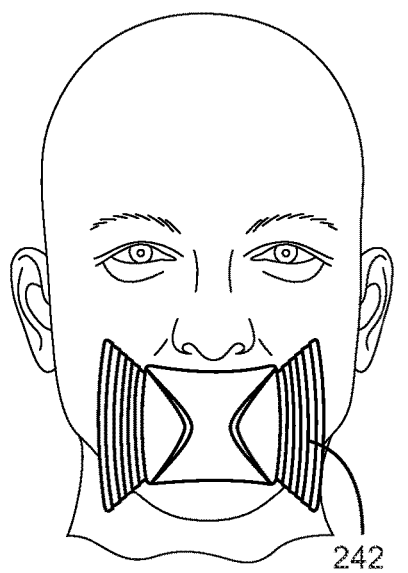
Figure 29C:
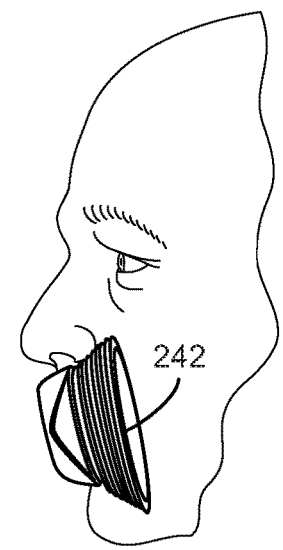
Figure 30A:
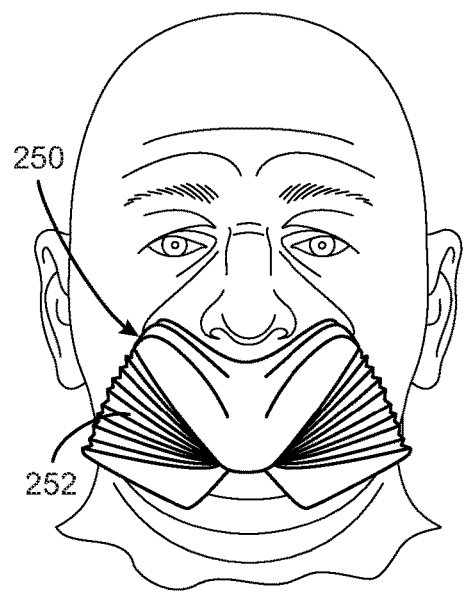
FIGS. 30A-C are depictions-of an alternative mouthpiece-type breathing apparatus having an adjustable dead space volume according to the present disclosure.
Figure 30B:
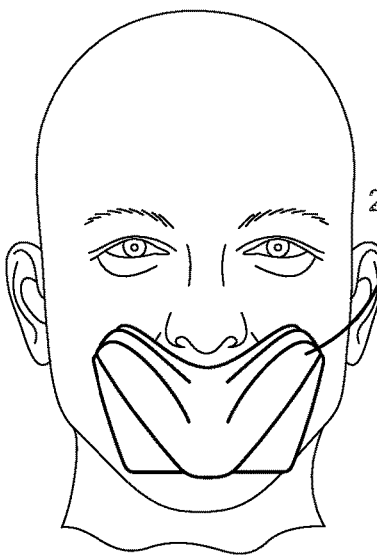
Figure 30C:
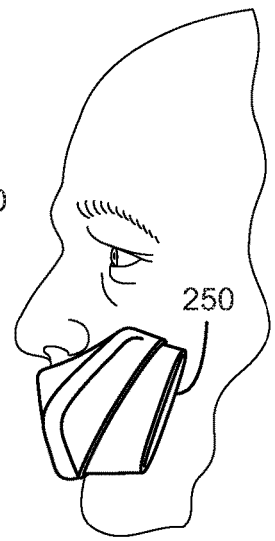
Figure 31A:
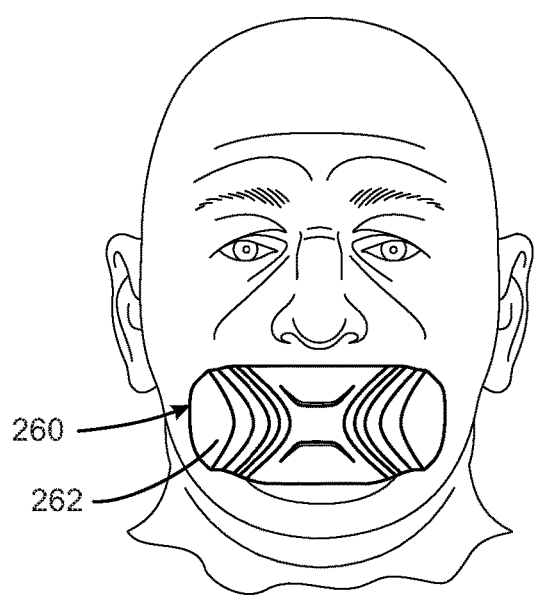
FIGS. 31A-B are depictions-of yet another mouthpiece-type breathing apparatus having an adjustable dead space volume according to the present disclosure.
Figure 31B:
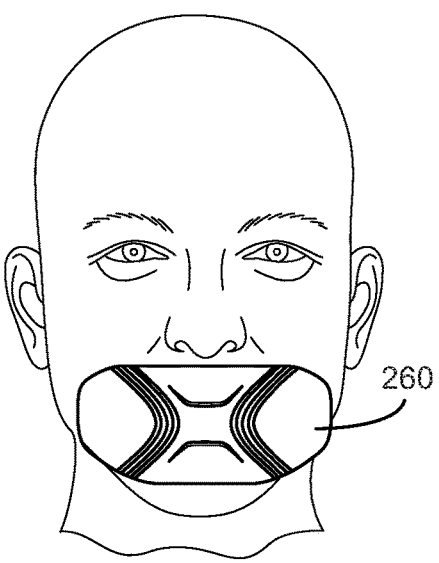

The breathing apparatus 220 shown in FIG. 25 includes a main chamber 221 similar to the main chambers in the prior embodiments. An adjustable wing chamber 222 is provided at each side of the main chamber, with an outlet 223 at the ends of each wing chamber. Each wing chamber 222 is divided into discrete chamber sections 224, with each section separably connected to an adjacent section. The adjacent sections can be connected at score lines 225 or perforations that permit easy separation of an outboard section from an inboard section. Each section can be marked with indicia indicating the total volume of the chamber up to and including the indicated chamber. Removing a particular chamber section 224 reduces the total volume, permitting adjustment of the dead space volume according to the particular user. A similar apparatus 226 is shown in FIGS. 26A-B in which multiple sections 227 can be separated in a similar manner to alter the dead space volume. It can be appreciated that the apparatuses 220, 226 can be modified so that the segments are separated by cutting the outboard segments away, rather than by separating along score lines or perforations. In this modification, the score lines can be modified to constitute indicator lines for cutting away segments to achieve a pre-defined dead space volume. The apparatus 228 shown in FIG. 27 A includes several peel-away segments 229 that can be removed down to a base segment 229a as shown in FIG. 27 B. The peel-away segments include tabs 229b that can be grasped to remove a particular segment together with all of the outboard segments to achieve a pre-defined dead space volume as described above.

FIGS. 28-32 show further embodiments of a breathing apparatus incorporating an accordion-type structure to expand the dead space of the apparatus. The breathing apparatus 230 shown in FIGS. 28A-C is similar to the apparatus of FIG. 21. The apparatus 230 includes a body 232 that includes a mouthpiece as discussed above. Two adjustable chambers 234 reintegrated to the base and include an outlet 235 at their ends. The chambers 234 are accordion configured so that the chambers can be expanded in fan-like fashion from the contracted configuration shown in FIG. 28B to the fully expanded position shown in FIG. 28A. The breathing apparatus 240 of FIGS. 29A-C is similar to the apparatus 230 except that the expandable chambers 242 expand and contract laterally, rather than fan-like, as shown in FIGS. 28A and 28B. The breathing apparatus 250 shown in FIGS. 30A-C is similar to the apparatus 230 except that the adjustable chambers 252 accordion laterally outward and slightly downward. The breathing apparatus 260 shown in FIGS. 31A-B is similar to the apparatus 240 in that the adjustable chambers 262 accordion laterally.

Figures 32A, 32B, 32C:
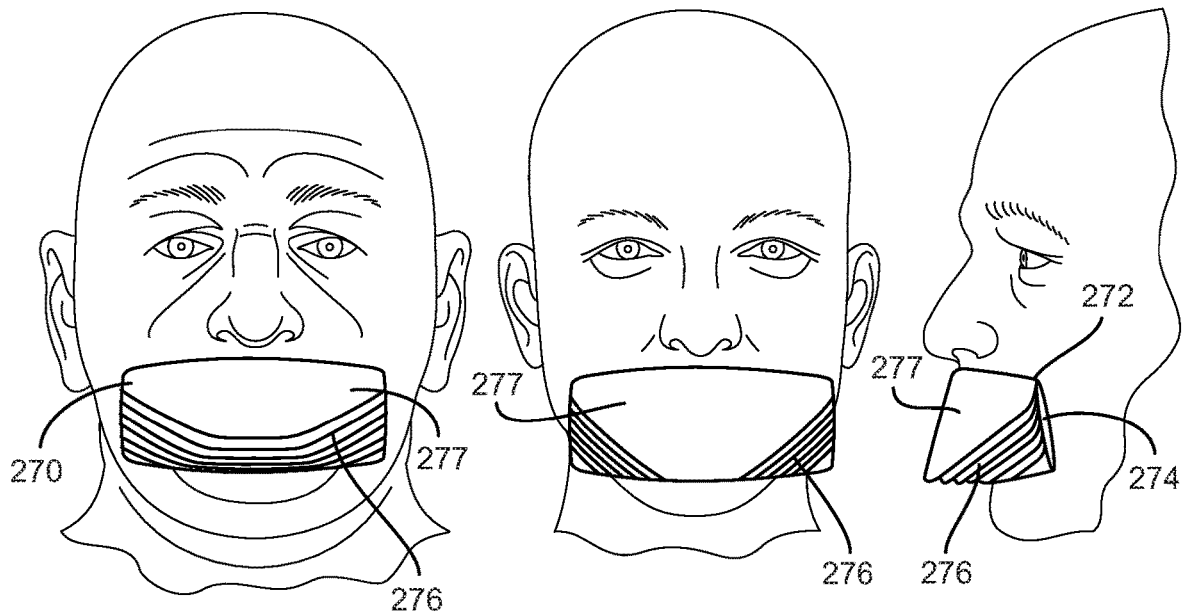
FIGS. 32A-C are depictions-of a further mouthpiece-type breathing apparatus having an adjustable dead space volume according to the present disclosure.

The breathing apparatus 270 of FIGS. 32A-C incorporates the accordion feature in a different manner. In this embodiment, the base 272 includes the mouthpiece feature discussed above, as well as the outlet 274. The adjustable chamber 276 accordions outward from the face of the person, as best shown in FIG. 32C. In particular, the upper panel 277 of the adjustable chamber 276 is pivoted upward to expand the chamber in accordion fashion.

Figure 33:
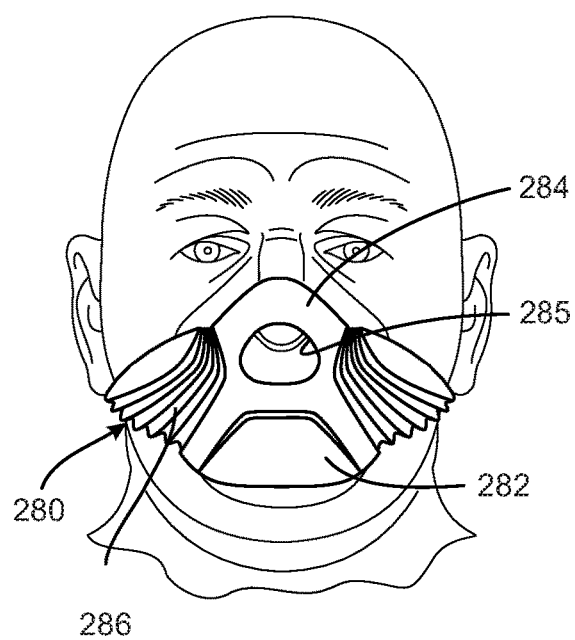
FIG. 33 is a depiction of an alternative mouthpiece-type breathing apparatus having an adjustable dead space volume according to the present disclosure.
Figure 34:
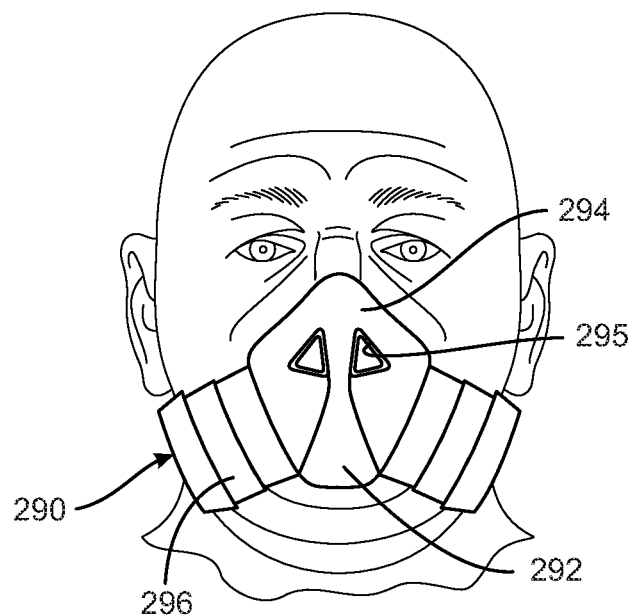
FIG. 34 is a depiction of yet another mouthpiece-type breathing apparatus having an adjustable dead space volume according to the present disclosure.
Figure 35:
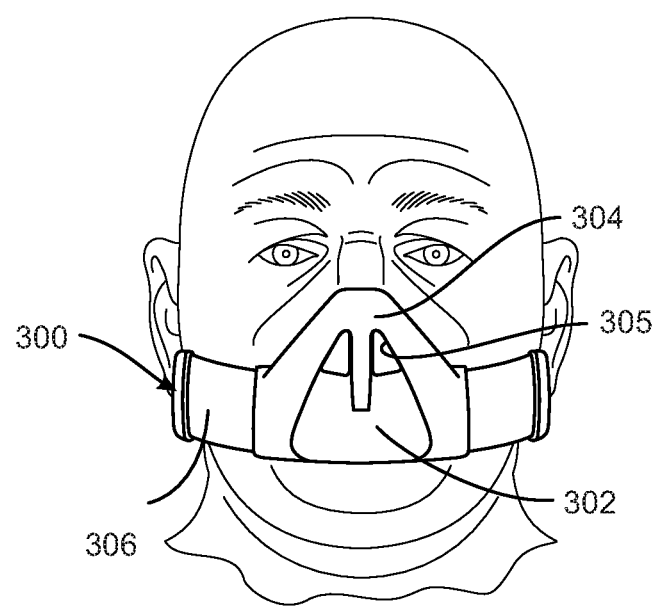
FIG. 35 is a depiction of a further mouthpiece-type breathing apparatus having an adjustable dead space volume according to the present disclosure.

The embodiments shown in FIGS. 19-32 incorporate a mouthpiece so that the apparatuses are supported by the lips and/or teeth of the person. The base and adjustable chambers of these embodiments are all positioned below the nose of the person. In the embodiments of FIGS. 33-35, the mouthpiece embodiments are modified to include a portion covering the nose of the person. Thus, the breathing apparatus 280 shown in FIG. 33 has a body 282 and adjustable chamber 286 that is similar to the embodiment of FIG. 28A. However, in this embodiment the apparatus 280 includes a nose portion 284 that extends over a portion of the person's nose. A breathing opening 285 is provided at the person's nostrils to permit nasal breathing as needed. This approach is incorporated into the apparatus 290 of FIG. 34 in which the base 292 and adjustable chambers 296 are similar to the embodiments of FIG. 22 or FIG. 24. In this case, the nose portion 294 includes separate openings 295 for each nostril. The breathing apparatus 300 of FIG. 35 includes a base 302 and adjustable chambers 306 similar to the embodiment of FIG. 10 with respect to the adjustment of the dead space by sliding the chamber 306 outward. Like the apparatus of FIG. 34, the nose portion 304 includes two openings 305 for nasal breathing.

The breathing apparatuses shown in FIGS. 4-35 are depicted in use by an adult human. However, it is understood that the overall dimensions of the apparatuses can be modified for use by infants or different age groups of children. For instance, the mouthpiece embodiment 230 of FIGS. 28A-C can be sized so that the body 232 is roughly the size of a conventional pacifier. The expandable chambers 234 can be appropriately sized for the different, and much smaller, dead space volumes necessary for an infant or child.

The breathing apparatuses shown in FIGS. 4-35 are configured to create a precise dead space at the user's mouth, with sufficient ventilation to permit normal respiration of the user, but with a controlled re-breathing of exhaled $CO_2$. The beneficial effects of increased $CO_2$ content in inhaled air, and more specifically the benefits of $pCO_2$ and hypercapnia, are described above. The breathing apparatuses allow for calibrated dead space in which a certain amount of exhaled $CO_2$ is retained to be combined with additional $CO_2$ in the next inhaled breath. In one feature of the present disclosure, the dead space produced by the breathing apparatuses are calibrated to achieve levels of inhaled $CO_2$ that lead to desirable levels of hypercapnia. The size of the dead space to achieve the desired amount of inhaled $CO_2$ is a function of the physiology of the user. In one specific aspect, the size of the dead space in the breathing apparatuses is a function of the tidal volume of air during respiration, which in turn is found to be a function of the weight of the user. One specific relationship is based on a formula for estimated tidal volume of a person, namely 3-9 ml per kg weight of the person. Another relationship described above multiplies the person's weight in kilograms by 7 to find the tidal volume in $cm^3$. With either approach, the desired dead space for rebreathing the $CO_2$ can be about ⅓ of the tidal volume. It is this volume that is used to adjust the breathing apparatus to match the physiology of the user.

Thus, the breathing apparatuses disclosed herein are configured to provide a dead space volume between the intake/outlet of the apparatus and the mouth of the user that, in effect, collects a certain amount of exhaled $CO_2$ and forces the user to re-breathe that $CO_2$ on the next inhalation. The dead space volume is established to be about ⅓ the tidal volume of the person. Since the tidal volume varies among individuals, the breathing apparatuses disclosed herein provide means for adjusting the dead space volume of the apparatus to meet the physiological needs of the user. In many circumstances it is not possible to determine the person's actual tidal volume, so the present disclosure contemplates the estimates discussed above to determine the desired dead space volume. Of course, if a tidal volume measurement for the person is available, that value can be used to more accurately generate the ⅓ tidal volume value to accurately define the dead space volume. nevertheless, in most cases the actual tidal volume will not be available, such as in a first responder scenario. The adjustable volume features of breathing apparatus, such as the apparatuses shown in FIGS. 4, 10-12 and 16, are well-suited for a first responder scenario since the volume adjustment feature is self-contained with the apparatus. For instance, the apparatus 10 of FIGS. 4-5 allows adjustment of the dead space volume by positioning the telescoping chamber portions 30, 32. These breathing apparatuses are further well-suited for a first responder scenario because they each include a strap arrangement to hold the breathing chamber at the mouth of the user/patient.

Some of the breathing apparatuses include a set or collection of chambers or tubes that are interchangeable on a base portion of the breathing apparatus. Such apparatuses include the breathing apparatuses shown in FIGS. 7-9, 13-15, 17 and 18. These apparatuses may be well-suited for use in a health care facility or hospital, where kits including multiple volume components can be readily stored.

Any of the face-mask embodiments of FIGS. 4-18 can be used on an outpatient basis to address various maladies, such as sleep apnea, sudden infant death syndrome (SIDS), dysautonomias, postural orthostatis tachycardia syndrome. The face-mask embodiments, as well as the mouthpiece embodiments of FIGS. 19-33 can be used by persons able to actively hold the mouthpiece portion of these breathing apparatuses. For instance, the mouthpiece embodiments can be used by persons in high G-force conditions, such as jet pilots, astronauts and various high-speed racing sports participants. The mouthpiece embodiments can also be useful to address returning from low-G conditions, such as occurs when an astronaut returns to normal gravity after spending a prolonged period in zero-G conditions.

Slosh absorption may also be reduced by reversibly increasing pressure or volume within the organs or cells of the organism. The intracranial volume and pressure can be reversibly increased by a device that reduces the flow of one or more outflow vessels of the cranium of said organism. This device would necessarily need to compress the vessels at a level surpassing venous pressure (approximately 15 mmHg, yet not surpass arterial pressure of approximately 80 mmHg). Intracranial volume can also be reversibly increased by the delivery of one or more medicaments to facilitate an increase in intracranial volume or pressure including but not limited to Minocycline, insulin-like growth factor 1, Provera, and Vitamin A. The breathing apparatuses described above can be used in conjunction with a device to reversibly increase intracranial volume and pressure. In particular, the active apparatuses shown in FIGS. 19-25 can be used with a collar-type device as described below.

In one embodiment, a compression device to reduce the likelihood of energy absorption to the brain is operable to raise intracranial and intra ocular volume and pressure by applying pressure to the outflow vasculature and/or cerebral spinal fluid of the brain. The result would be an increase in the structure's coefficient of restitution (r) by attaching a cinch or collar around the neck of the individual or organism. The compression device can be of any design including, but not limited to, a band or cord.

Safely and reversibly increasing cerebral blood volume by any amount up to 10 $cm^3$ and pressure by any amount up to 70 mmHg would serve to fill up the compliance of the cerebral vascular tree and thus reduce the ability to absorb external energies through slosh energy absorption. "With the application of measured pressure to the neck, the cranial blood volume increases rapidly and plateaus at a new higher level. Moyer et al reported that cerebral arterial blood flow was not affected by obstructing the venous outflow of blood from the brain." See, *Effect of Increased Jugular Pressure on Cerebral Hemodynamics*, J. H. Moyer. S. I. Miller, and H. Snyder, 1 Appl. Physiol. 7:245, 1954, the entire disclosure of which is incorporated herein by reference. "The blood volume venous pressure relationship shows a diminishing increase in volume with each increment of neck pressure over the range 40 to 70 mm of mercury. It is of interest that the cranial blood volume increases from 10 to 30 percent (with this neck pressure). See, *The Elasticity of the Cranial Blood Pool*, Masami Kitano, M.D., and William H. Oldendorf, M.D. and Benedict Cassen, Ph.D., Journal Of Nuclear Medicine, 5: 613-625, 19 64, the entire disclosure of which is incorporated herein by reference. The cerebral spinal fluid pressure responds on compression of the individual jugular veins. The average rise was 48 percent. See, *Observations on the C.S.F Pressure during Compression of the Jugular Veins*, D. A. J. Tyrrell, Postgrad. Med. J 1951; 27; 394-395, the entire disclosure of which is incorporated herein by reference. Jugular compression increases cerebral blood flow to a new plateau in as little as 0.5 seconds. See, *The Elasticity of the Cranial Blood Pool*, Masami Kitano, M.D., and William H. Oldendorf, M.D.:C and Benedict Cassen, Ph.D., Journal Of Nuclear Medicine, 5: 616, 19 64; A *Cinemyelographic Study of Cerebro Fluid Dynamics*, Amer J of Roent, GILLAND et al. 10 6 (2): 3 69 (1969), the entire disclosures of which are incorporated herein by reference. This degree of cranial blood volume and pressure increase would be very beneficial in slosh mitigation. Although lesser cranial pressure and volume increases may still have beneficial effects, an increase of 3 cm$^3$ volume and 5 mm Hg is a baseline goal.

Further, safety of such a procedure of venous compression is quite abundant in the literature as it mirrors the 100 year old Quenkenstadt Maneuver. In this maneuver, "the compression of the neck does not interfere with arterial flow into the cranium. Although the venous jugular flow beneath the pressure cuff may be temporarily halted, the venous outflow from the cranium is never completely stopped, particularly from the anastomosis between the spinal vein and the basilar plexus and occipital sinuses which are incompressible. See, *Anatomical Problems Concerned in the Study of Cerebral Blood Flow*, VO. V. Batson, Fed. Proc. 3:139, 1944; *Experimental Approaches to the Study of the Cerebral Circulation*, D. E. Gregg and R. E. Shipley, Fed. Proc. 3:144, 1944, the entire disclosures of which are incorporated herein by reference. In fact, there was no correlation between electroencephalographic (EEG) changes or changes in systolic arterial blood pressure occurring during jugular compression. See, *Changes in the electroencephalogram and in systemic blood pressure associated with carotid compression*, Fernando Tones, M.D. and Anna Ellington, M.D., Neurology, 1970; 20:1077, the entire disclosure of which is incorporated herein by reference. Thus, neck compression of up to 70 mmHg does not affect cardiac output, arteriolar blood pressure, pulse rate, or urine flow.

The compression device may be of any material including but not limited to elastic materials. Elastic materials can be any material which when stretched will attempt to return to the natural state and can include one or more of textiles, films (wovens, nonwovens and nettings), foams and rubber (synthetics and natural), polychloroprene (e.g. Neoprene), elastane and other polyurethane-polyurea copolymerss (e.g. Spandex, Lycra), fleece, warp knits or narrow elastic fabrics, raschel, tricot, milanese knits, satin, twill, nylon, cotton tweed, yams, rayon, polyester, leather, canvas, polyurethane, rubberized materials, elastomers, and vinyl. There are also a number of elastic materials which are breathable or moisture wicking which may be preferable during extended wearing periods or wearing during periods of exercise. In addition the compression device could be partially constructed, coated, or constructed of one or more protecting materials such as Kevlar (para-aramid synthetic fibers), Dyneema (ultra-high-molecular-weight polyethylene), ceramics, or shear thickening fluids.

The device may encompass circumferentially, the entire neck or just partially around the neck, yet still providing partial or total occlusion of one or more of the outflow vessels on the neck, specifically, but not limited to the internal and external jugular veins, the vertebral veins, and the cerebral spinal circulation. The device may encompass horizontally, the entire neck or just partially up and down the neck.

The width of the compression device may range from a mere thread (at a fraction of an inch) to whatever the length of the exposed neck (up to 12 inches in humans or greater in other creatures), the length may range from 6 to 3 6 inches to circumnavigate the neck. The width of the compression device could be as small as 114 inch but limited only by the height of the neck in largest width, which would be typically less than 6 inches. The thickness of said device could range from a film being only a fraction of a millimeter to a maximum of that which might be cumbersome yet keeps ones neck warm such as 2-3 inches.

The compression device may be preformed for the user in a circular construct. This one size fits all style can have a cinch of sorts that allows one to conform the device to any neck region. Alternatively the compression device may be a first and second end which is connected by a fastener. A fastener may be a hook and ladder attachment, a snap, a button or any of a number of attachment mechanisms that would be known to one skilled in the art. A compression device with a fastener could have a release mechanism whereby the device can break open or apart at a predetermined force to prevent the collar from inadvertently being snagged or compressing too tightly. One quick release or automatic release method would be the applying of small amounts of hook and ladder attachments within the circumferential ring which would shear apart upon too much force being applied to the compression device.

The compression device may also have one or more monitoring devices and/or communication devices attached or embedded. The compression device can also have a pocket or pouch attached depending on the height of the compression device used. Certainly, advertising can be imprinted or emblazoned onto the device.

These terms and specifications, including the examples, serve to describe the invention by example and not to limit the invention. It is expected that others will perceive differences, which, while differing from the forgoing, do not depart from the scope of the invention herein described and claimed. In particular, any of the function elements described herein may be replaced by any other known element having an equivalent function.

What is claimed is:

1. A breathing apparatus for increasing the partial pressure of carbon-dioxide ($CO_2$) in the blood of a subject ($pCO_2$), comprising:
   a chamber having an opening configured to be in direct communication with the mouth of the subject and at least one outlet configured to be in direct communication with ambient air for gas to flow therethrough as the subject inhales the ambient air and exhales $CO_2$ through said at least one outlet; and an enlarged dead space between said opening and each of said at least one outlet, the dead space defining a volume sized to retain a predetermined portion of the $CO_2$ exhaled by the subject as the subject exhales through each of said at least one outlet, so that the predetermined portion is mixed within the enlarged dead space with ambient air inhaled through each of said at least one outlet by the subject on the next inhalation, wherein the volume of the dead space is 10 to 50% of the tidal volume of air displaced by the subject during inhalation and exhalation.

2. The breathing apparatus of claim 1, further comprising a portion configured for retaining the breathing apparatus in direct communication with the mouth of the subject when in use.

3. The breathing apparatus of claim 2, wherein said portion for retaining the breathing apparatus includes a strap arrangement for supporting the breathing apparatus on the head of the subject.

4. The breathing apparatus of claim 2, wherein said portion for retaining the breathing apparatus includes a mouthpiece configured to be clamped between the teeth or lips of the subject to support the breathing apparatus at the mouth of the subject when in use.

5. The breathing apparatus of claim 1, wherein the dead space volume is sized in relation to the weight of the subject.

6. The breathing apparatus of claim 5, wherein the enlarged dead space is defined by at least one bellows-configured component, an outboard end of said bellows-configured component defining said outlet and an inboard end of said bellows-configured component in communication with said chamber, wherein said bellows-configured component is extendable to increase the dead space volume and retractable to decrease the dead space volume.

7. The breathing apparatus of claim 5, wherein said enlarged dead space is defined by an elongated chamber having one end in communication with said opening and an opposite end defining said at least one outlet, said elongated chamber including a plurality of discrete chamber sections, each section separably connected to an adjacent chamber section.

8. The breathing apparatus of claim 7, wherein the discrete chamber sections are connected by a feature facilitating tearing of said elongated chamber to remove an outermost chamber section.

9. The breathing apparatus of claim 1, wherein the volume of the dead space is adjustable.

10. The breathing apparatus of claim 9, wherein the enlarged dead space is defined by at least one pair of telescoping hollow cylinders, one of the pair of cylinders defining said opening and the other of the pair defining said at least one outlet.

11. The breathing apparatus of claim 10, wherein one of the cylinders includes indicia indicative of the volume enclosed by the pair telescoping cylinders at a particular relationship of the telescoping cylinders relative to each other, and the other of the pair of cylinders includes a feature for marking the indicia.

12. The breathing apparatus of claim 11, wherein said feature for marking includes a ring disposed at a distal end of said other of the pair of cylinders.

13. The breathing apparatus of claim 12, wherein said other of said pair of cylinders is telescopingly disposed within said one of the cylinders, and said ring is a sliding seal for sealing engagement between said pair of cylinders.

\* \* \* \* \*